(12) United States Patent
Takahashi et al.

(10) Patent No.: US 11,419,484 B2
(45) Date of Patent: Aug. 23, 2022

(54) PACKAGE OF MOUNTING JIG MOUNTED BALLOON AND BALLOON MOUNTING METHOD

(71) Applicant: FUJIFILM Corporation, Tokyo (JP)

(72) Inventors: Nobuharu Takahashi, Kanagawa (JP); Ayumu Kawashima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 288 days.

(21) Appl. No.: 16/816,287

(22) Filed: Mar. 12, 2020

(65) Prior Publication Data

US 2020/0305694 A1     Oct. 1, 2020

(30) Foreign Application Priority Data

Mar. 28, 2019  (JP) .............................. JP2019-063242
Feb. 14, 2020  (JP) .............................. JP2020-023742

(51) Int. Cl.
| | |
|---|---|
| *A61B 1/00* | (2006.01) |
| *A61B 1/005* | (2006.01) |
| *A61B 1/06* | (2006.01) |
| *A61B 1/01* | (2006.01) |

(52) U.S. Cl.
CPC ........ *A61B 1/00135* (2013.01); *A61B 1/0055* (2013.01); *A61B 1/00082* (2013.01); *A61B 1/00091* (2013.01); *A61B 1/00101* (2013.01); *A61B 1/01* (2013.01); *A61B 1/06* (2013.01)

(58) Field of Classification Search
None
See application file for complete search history.

(56) References Cited

U.S. PATENT DOCUMENTS

2005/0125005 A1* 6/2005 Fujikura ........... A61M 25/1027
                                                              606/116

FOREIGN PATENT DOCUMENTS

| | | |
|---|---|---|
| JP | 2005230084 | 9/2005 |
| JP | 2009011656 | 1/2009 |

* cited by examiner

*Primary Examiner* — Timothy J Neal
(74) *Attorney, Agent, or Firm* — JCIPRNET

(57) ABSTRACT

Provided are a package of a mounting jig mounted balloon and a balloon mounting method capable of reducing the burden of an operation of mounting a balloon in an insertion part of an endoscope.
A balloon includes a first sleeve part, a second sleeve part, and a balloon main body. A balloon mounting jig is formed to be folded flat in a hollow cylindrical shape, and has a main body having a first opening part and a second opening part, and a pair of guide pieces that is provided on the second opening part and face each other. A package of a mounting jig mounted balloon is configured so that the balloon mounting jig and the balloon are contained in the container, in which in the container, the balloon is disposed so that the second sleeve part is disposed inside the folded balloon main body and the pair of guide pieces is disposed inside the first sleeve part and the second sleeve part.

15 Claims, 21 Drawing Sheets

PACKAGE OF MOUNTING JIG MOUNTED BALLOON AND BALLOON MOUNTING METHOD

CROSS-REFERENCE TO RELATED APPLICATIONS

The present application claims priority under 35 U.S.C. § 119 to Japanese Patent Application No. 2019-063242 filed on Mar. 28, 2019 and Japanese Patent Application No. 2020-023742 filed on Feb. 14, 2020. Each of the above applications is hereby expressly incorporated by reference, in its entirety, into the present application.

BACKGROUND OF THE INVENTION

1. Field of the Invention

The present invention relates to a package of a mounting jig mounted balloon and a balloon mounting method, and more particularly, to a package of a mounting jig mounted balloon and a balloon mounting method for mounting a balloon to an insertion part of an endoscope.

2. Description of the Related Art

In endoscope apparatuses, balloons that expand and contract are used in various applications. For example, in an endoscope apparatus for observing a deep digestive tract such as the small intestine or the large intestine, an inflatable balloon is mounted to an insertion part of an endoscope, and it is possible to fix the insertion part of the endoscope inside the body by expanding the balloon.

Such a balloon is made of an elastic body such as rubber, and its end portion is formed in a cylindrical shape having a smaller diameter than an outer diameter of a mounting target (the insertion part of the endoscope) in a natural state. Further, in mounting the balloon, after covering the mounting target with the balloon while expanding the diameter of the end portion of the balloon, the end portion of the balloon is fixed to the mounting target by winding a thread from the top of the end portion of the balloon or mounting a rubber band onto the end portion of the balloon.

However, there is a problem that an operation of covering the mounting target with the balloon while expanding the diameter of the end portion of the balloon is very troublesome and takes time and efforts. For example, JP2005-230084A discloses a balloon mounting jig having a retaining part that retains an opening part of a balloon inserted into a lumen of a mounting jig main body at both end portions of the mounting jig main body. The balloon mounting jig retains the opening part of the balloon at the retaining part of the mounting jig main body, and is externally fit onto the insertion part of the endoscope in a state where the balloon is in a close contact with the mounting jig main body, and the balloon is mounted in the insertion part of the endoscope.

Further, JP2009-011656A discloses a balloon mounting jig including first and second guide pieces that are inserted into sleeve parts that are provided at both end portions of a balloon main body. The balloon mounting jig is configured so that an insertion part of an endoscope is inserted between the first guide piece and the second guide piece to insert an endoscope into the sleeve parts of the balloon.

SUMMARY OF THE INVENTION

However, in the mounting jig disclosed in JP2005-230084A and JP2009-011656A, a balloon put in a pack is mounted to the mounting jig by a manual operation, and then, is mounted in the insertion part of the endoscope. This operation is performed with gloves to maintain a sterility state of the balloon, which is troublesome and time-consuming. Further, since the balloons are randomly placed in the pack, the balloons are contained in the pack in a state of being closely attached to each other by stickiness (tack) on the surface of the balloon. For this reason, it is necessary to carefully separate the balloon before mounting the balloon in the endoscope, which is also a time-consuming factor.

The present invention has been made in consideration of the above-mentioned problems, and an object of the invention is to provide a package of a mounting jig mounted balloon and a balloon mounting method capable of reducing the burden of an operation of mounting a balloon in an insertion part of an endoscope.

In order to achieve the object of the invention, there is provided a package of a mounting jig mounted balloon in which a balloon mounting jig for mounting a balloon in an insertion part of an endoscope and the balloon are contained in a container, in which the balloon includes a first sleeve part provided at one end thereof, a second sleeve part provided at the other end thereof, and a balloon main body provided between the first sleeve part and the second sleeve part, the balloon mounting jig includes a main body that is formed in a hollow cylindrical shape to be folded flat and has a first opening part at one end thereof and a second opening part at the other end thereof, and a pair of guide pieces that faces each other and is provided so as to extend from the second opening part toward a side opposite to a side where the first opening part is provided, and inside the container, the balloon is disposed so that the balloon main body is folded inwardly and the second sleeve part is disposed inside a folded opening part formed in a folded portion of the balloon, and the balloon mounting jig is disposed so that the pair of guide pieces and at least a part of the main body are inserted from the folded opening part and the pair of guide pieces is disposed inside the first sleeve part and the second sleeve part.

In order to achieve the object of the invention, there is provided a balloon mounting method using the package of the mounting jig mounted balloon of the present invention, the method comprising: inserting the insertion part of the endoscope into the main body from the first opening part; inserting the insertion part of the endoscope between the pair of guide pieces and inserting the insertion part of the endoscope into the first sleeve part and the second sleeve part through the pair of guide pieces; extracting the balloon, the balloon mounting jig, and the insertion part of the endoscope from the container; moving the second sleeve part and the balloon mounting jig to a proximal end side of the insertion part of the endoscope in a state where the first sleeve part is fixed to the insertion part of the endoscope; and removing the balloon mounting jig from the second sleeve part and mounting the balloon on the insertion part of the endoscope.

According to the package of the mounting jig mounted balloon of the invention, as the balloon main body is folded back inwardly and the second sleeve part is disposed inside the folded opening part in the container, and thus, it is possible to contain the balloon and the balloon mounting jig in a state where the pair of guide pieces of the balloon mounting jig is inserted into the first sleeve part and the second sleeve part.

Further, according to the balloon mounting method using the package of the mounting jig mounted balloon, by inserting the insertion part of the endoscope from the first opening part of the balloon mounting jig, it is possible to insert the insertion part of the endoscope into the first sleeve part and the second sleeve part through the pair of guide pieces. Then, by extracting the balloon, the balloon mounting jig, and the insertion part of the endoscope from the container and moving the second sleeve part together with the balloon mounting jig, it is possible to move the second sleeve part to a predetermined position, and to easily perform mounting of the balloon into the endoscope.

DESCRIPTION OF THE PREFERRED EMBODIMENTS

Hereinafter, a package of a mounting jig mounted balloon, a balloon mounting method according to an embodiment of the present invention will be described with reference to the accompanying drawings.

Figure 1:
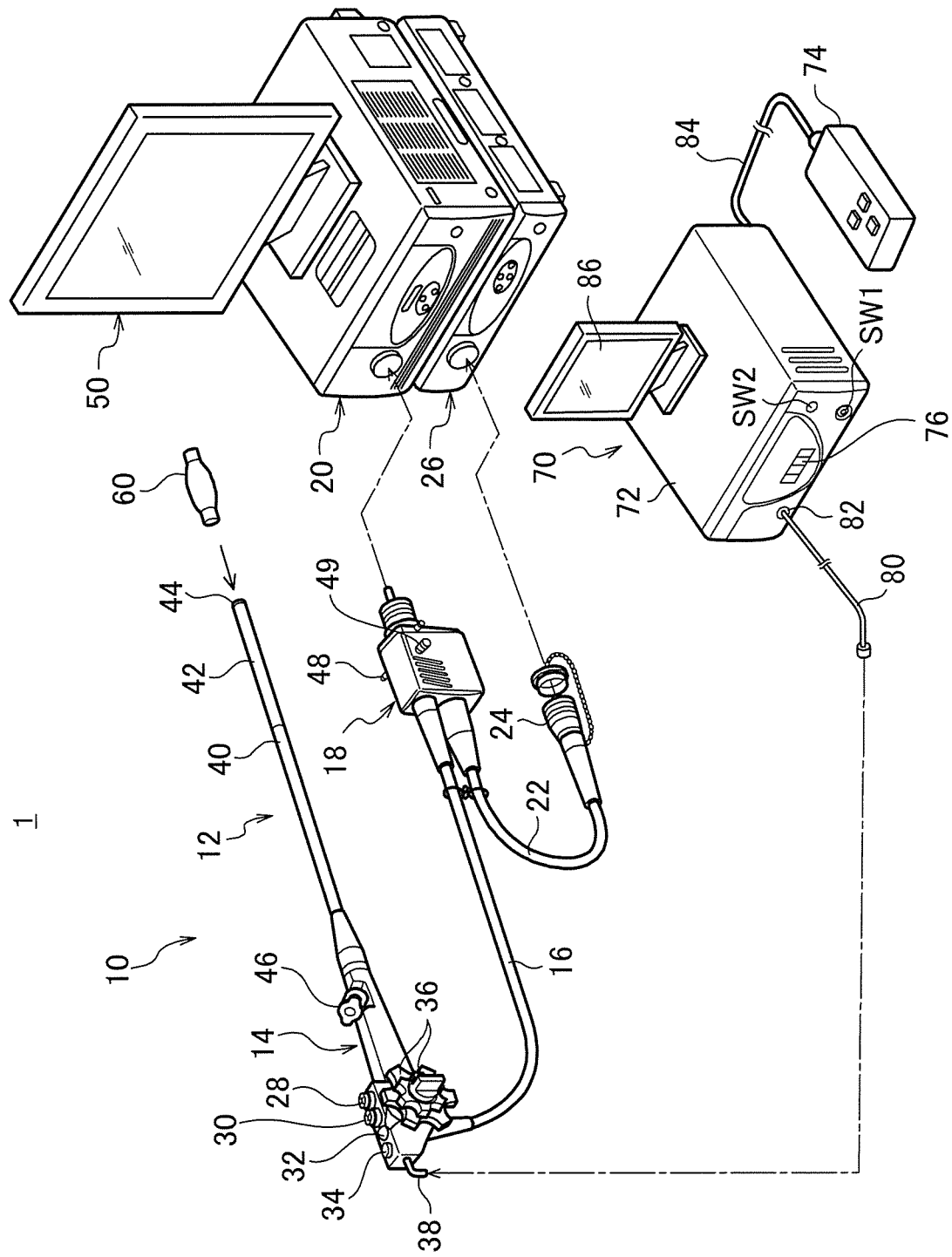
FIG. 1 is a diagram showing a system configuration of an endoscope apparatus using a balloon.

FIG. 1 is a system configuration diagram showing an example of an endoscope apparatus using a balloon contained in a package of a mounting jig mounted balloon according to the embodiment of the present invention. As shown in FIG. 1, the endoscope apparatus mainly includes an endoscope 10, a balloon 60, and a balloon control device 70 as main components.

The endoscope 10 includes an operation part 14 and an insertion part 12 that is connected to the operation part 14 and is inserted into the body. A universal cord 16 is connected to the operation part 14, and an LG connector 18 is provided at a distal end of the universal cord 16. The LG connector 18 is detachably connected to a light source device 20, and thus, illumination light is sent to an illumination window (not shown) provided at the distal end of the insertion part 12. Further, an electric connector 24 is connected to the LG connector 18 through a cable 22, and the electric connector 24 is detachably connected to a processor 26.

An air/water supply button 28, a suction button 30, a shutter button 32, and a function switching button 34 are provided in parallel in the operation part 14, and a pair of angle knobs 36 and 36 is also provided therein.

The insertion part 12 includes a flexible part 40, a bending part 42, and a distal end part 44 in order from the side of the operation part 14. The flexible part 40 is configured by covering an outer periphery of a metal plate wound in a spiral shape with a net and coating the outer periphery, and has sufficient flexibility.

The bending part 42 is configured to be bent remotely by rotating the angle knobs 36 and 36 of the operation part 14. For example, the bending part 42 is configured so that a plurality of cylindrical nodal rings are connected to be rotatable using pins and a plurality of operation wires are inserted into the nodal rings to be guided by the pins. Further, by pushing and pulling the operation wires, the nodal rings are rotated to bend the bending part 42. By bending the bending part 42, it is possible to direct the distal end part 44 in a desired direction.

Figure 2:
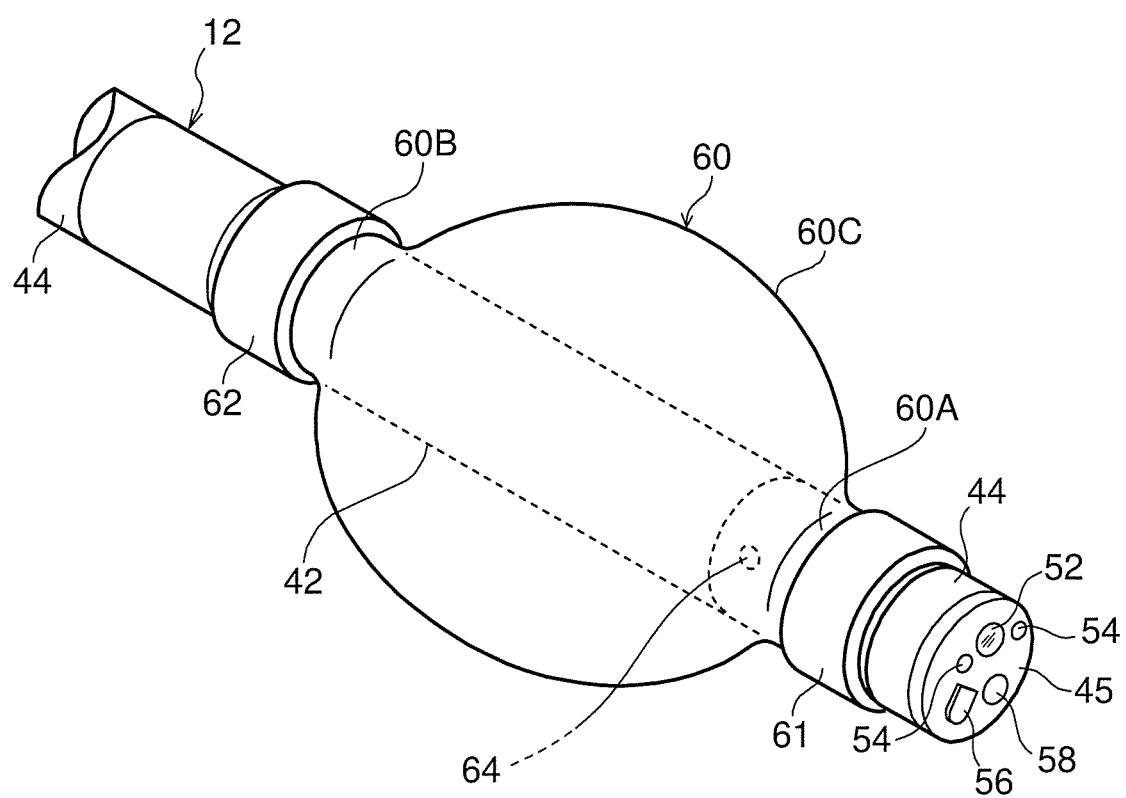
FIG. 2 is a perspective view showing a distal end part of an insertion part of an endoscope.

As shown in FIG. 2, an observation window 52, illumination windows 54 and 54, an air/water supply nozzle 56, and a forceps port 58 are provided on a distal end surface of the distal end part 44. An observation optical system and an imaging element such as a complementary metal oxide semiconductor (CMOS) and a charge coupled device (CCD) are disposed behind the observation window 52, and a signal cable is connected to a substrate that supports the imaging element. The signal cable is inserted into the insertion part 12, the operation part 14, the universal cord 16, and the like to be extended to the electric connector 24, and is connected to the processor 26. Accordingly, an observation image received by the observation window 52 is formed on a light receiving surface of the imaging element, and is converted into an electric signal. The electric signal is output to the processor 26 through the signal cable and is converted into a video signal. Thus, the observation image is displayed on the monitor 50 connected to the processor 26.

The illumination window 54 is configured so that an illumination optical system and an emitting end of a light guide (not shown) are disposed behind the illumination window 54. The light guide is inserted into the insertion part 12, the operation part 14, and the universal cord 16, and an incident end of the light guide is disposed in the LG connector 18. Accordingly, by connecting the LG connector 18 to the light source device 20, illumination light emitted from the light source device 20 is transmitted to the illumination optical system through the light guide and is emitted forward from the illumination window 54.

The air/water supply nozzle 56 provided at the distal end part 44 communicates with a valve (not shown) operated by the air/water supply button 28. The valve communicates with an air/water supply connector 48 provided in the LG connector 18. An air/water supply device (not shown) is connected to the air/water supply connector 48 to supply air and water. Accordingly, by operating the air/water supply button 28, air or water is jetted from the air/water supply nozzle 56 toward the observation window 52.

The forceps port 58 provided at the distal end part 44 communicates with a forceps insertion part 46. Accordingly, by inserting a treatment tool such as a forceps through the forceps insertion part 46, it is possible to draw out a treatment tool from the forceps port 58. Further, the forceps port 58 communicates with a valve (not shown) operated by the suction button 30, and the valve is connected to the suction connector 49 of the LG connector 18. Accordingly, by connecting a suction device (not shown) to the suction connector 49 and performing an operation using the suction button 30, it is possible to suction a lesion portion or the like through the forceps port 58.

The balloon 60 is detachably mounted on the outer periphery of the insertion part 12 of the endoscope 10. The balloon 60 is made of an elastic material such as silicone rubber. The balloon 60 includes a first sleeve part 60A provided at one end thereof, a second sleeve part 60B provided at the other end thereof, and a balloon main body 60C provided between the first sleeve part 60A and the second sleeve part 60B, in which the first sleeve part 60A and the second sleeve part 60B are formed in an approximately cylindrical shape that is narrowed with respect to the balloon main body 60C.

The balloon 60 is disposed at a predetermined mounting position (for example, from the distal end part 44 to the bending part 42) by causing the insertion part 12 to pass therethrough. The first sleeve part 60A and the second sleeve part 60B are formed to have an inner diameter smaller than an outer diameter of the insertion part 12 of the endoscope 10 in a natural state. In a case where the balloon 60 is mounted on the insertion part 12, an elastic force of the first sleeve part 60A and an elastic force of the second sleeve part 60B act inward in a radial direction of the insertion part 12. The balloon 60 is retained at a predetermined position of the insertion part 12 by the elastic forces.

A rubber band that is a cylindrical first balloon fixing member 61 is mounted on an outer periphery of the first sleeve part 60A, and a rubber band that is a cylindrical second balloon fixing member 62 is mounted on an outer periphery of the second sleeve part 60B. The balloon 60 is fixed to the insertion part 12 by the first balloon fixing member 61 and the second balloon fixing member 62. The package of the mounting jig mounted balloon according to the embodiment of the present invention includes the balloon 60 and the balloon mounting jig for mounting the balloon 60 to the insertion part 12, which will be described later.

A ventilation hole 64 is formed at the balloon mounting position of the insertion part 12, and the ventilation hole 64 communicates with a balloon air supply port 38 of the operation part 14 shown in FIG. 1. A tube 80 shown in FIG. 1 is connected to the balloon air supply port 38, and the balloon control device 70 is connected through the tube 80. The balloon control device 70 is a device that supplies and suctions fluid such as air into the balloon 60. By supplying and suctioning fluid (for example, air) from the balloon control device 70, it is possible to supply and suction air into the balloon 60. The balloon 60 expands into a substantially spherical shape by being supplied with air, and sticks to the outer surface of the insertion part 12 by suctioning air.

As shown in FIG. 1, the balloon control device 70 includes a device main body 72 and a hand switch 74 for remote control, as main components. On a front surface of the device main body 72, a power switch SW1, a stop switch SW2, and a pressure display unit 76 are provided. The pressure display unit 76 is a panel that displays a pressure value of the balloon 60, and an error code is displayed on the pressure display unit 76 in a case where an abnormality such as balloon breakage occurs.

The tube 80 that performs the supply and suction of air into the balloon 60 is connected to the front surface of the device main body 72. A connection portion between the tube 80 and the device main body 72 is provided with a backflow prevention unit 82 for preventing backflow of a body fluid in a case where the balloon 60 is broken. The backflow prevention unit 82 is configured by incorporating a gas-liquid separation filter in a hollow disk-like case (not shown) that is detachably mounted to the device main body 72, in which inflow of fluid in the device main body 72 is prevented by the filter.

On the other hand, the hand switch 74 is provided with various switches. For example, a stop switch similar to the stop switch SW2 on the device main body 72, an ON/OFF switch for instructing pressurization and decompression of the balloon 60, a pause switch for retaining the pressure of the balloon 60, and the like are provided. The hand switch 74 is electrically connected to the device main body 72 through a cord 84. Although not shown in FIG. 1, the hand switch 74 is provided with a display unit that indicates an air supply state or an exhaust state of the balloon 60.

The balloon control device 70 causes air to be supplied to the balloon 60 to expand the balloon 60, and controls the air pressure at a predetermined value to retain the balloon 60 in an expanded state. Further, the balloon control device 70 causes air to be suctioned from the balloon 60 to contract the balloon 60, and controls the air pressure at a predetermined value to retain the balloon 60 in a contracted state.

The balloon control device 70 is connected to a balloon dedicated monitor 86, and displays the pressure value and the expanded and contracted state of the balloon 60 on the balloon dedicated monitor 86 in a case where the balloon 60 is expanded and contracted. The pressure value and the expanded and contracted state of the balloon 60 may be displayed on the monitor 50 to be superimposed on the observation image of the endoscope 10.

As an example of the operation method of the endoscope apparatus, the insertion part 12 is inserted in a pushing manner, and the balloon 60 is expanded as necessary to fix the insertion part 12 in the body (for example, the large intestine). Further, after the insertion part 12 is pulled to simplify a tubular shape of the body (for example, the large intestine), the balloon 60 is contracted and the insertion part 12 is further inserted into a deep portion of the intestinal tract. For example, the insertion part 12 is inserted from the subject's anus, and in a case where the distal end of the insertion part 12 passes the sigmoid colon, the balloon 60 is expanded to fix the insertion part 12 to the intestinal tract, and the insertion part 12 is pulled to form the sigmoid colon in a substantially linear shape. Further, the balloon 60 is contracted and the distal end of the insertion part 12 is inserted into a deep portion of the intestinal tract. In this way, it is possible to insert the insertion part 12 in the deep portion of the intestinal tract. The above-described endoscope 10 may be used as a double balloon type endoscope apparatus together with an insertion auxiliary tool (not shown) with a balloon attached thereto.

Package of Mounting Jig Mounted Balloon

Next, the package of the mounting jig mounted balloon according to the present embodiment will be described. The package of the mounting jig mounted balloon is used for easily mounting the balloon 60 to the insertion part 12 of the endoscope 10. The package of the mounting jig mounted balloon is configured so that a balloon mounting jig for mounting the balloon 60 to the insertion part 12 of the endoscope 10 and the balloon 60 are contained in a container.

The first sleeve part 60A and the second sleeve part 60B of the balloon 60 have an inner diameter smaller than the outer diameter of the insertion part 12 in a natural state, and it is difficult to cause the insertion part 12 to pass therethrough in the natural state. According to the package of the mounting jig mounted balloon according to the embodiment of the present invention, since the balloon mounting jig and the balloon are contained in the container in a state where the balloon mounting jig is mounted to the balloon, it is possible to omit an operation of mounting the balloon mounting jig to the balloon. Further, it is possible to easily mount the balloon to the endoscope using the balloon mounting jig, to thereby reduce the burden of an operator. Here, the natural state refers to a state where no external force is applied. In this state, the first sleeve part 60A and the second sleeve part 60B are not expanded and contracted.

Balloon Mounting Jig

Figure 3:
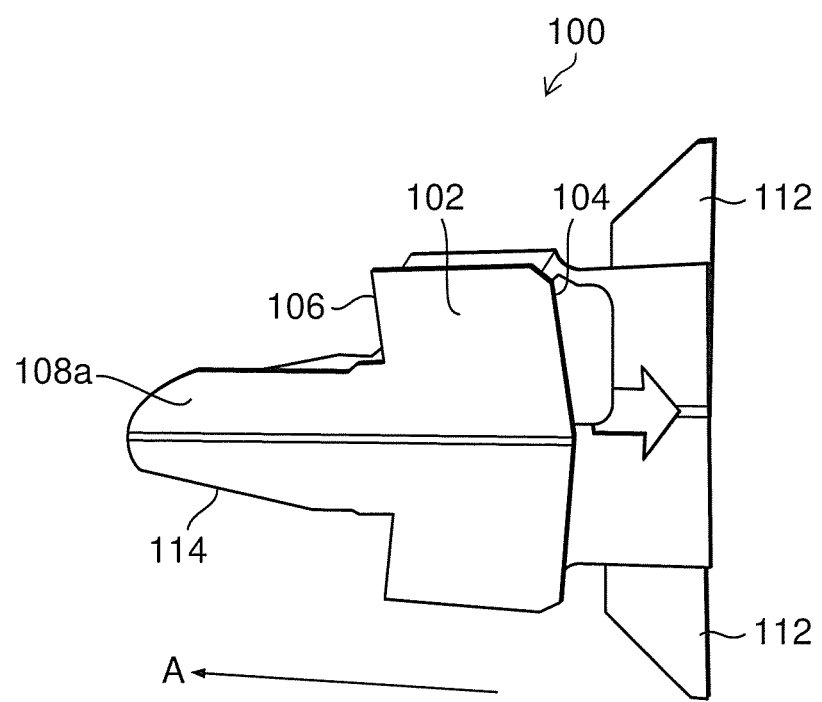
FIG. 3 is a plan view of a balloon mounting jig.
Figure 4:
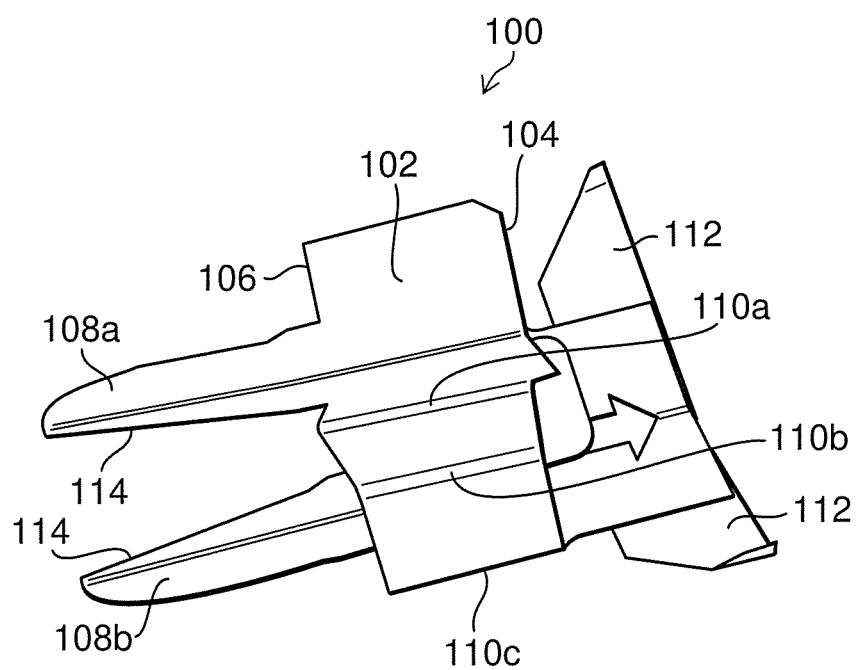
FIG. 4 is a perspective view showing a main body in a state where a first opening part and a second opening part are opened.
Figure 5:
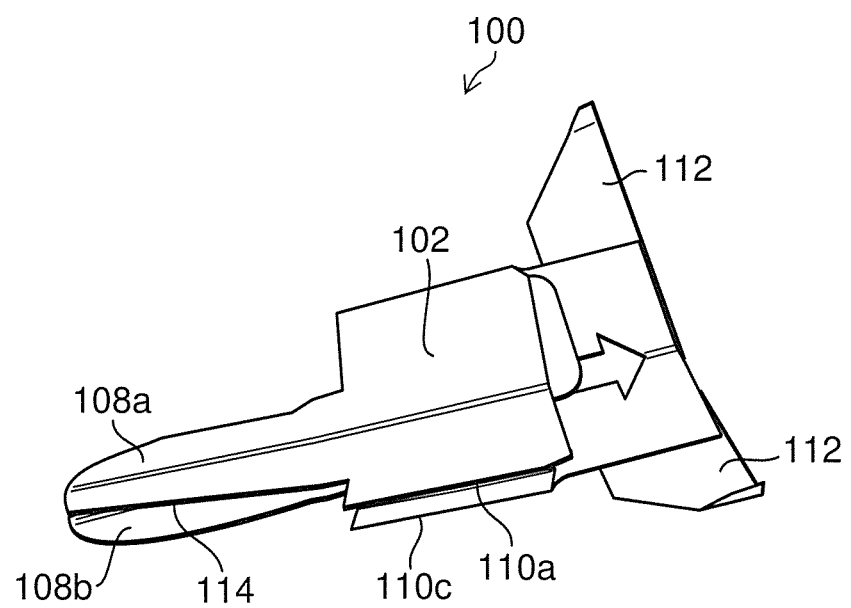
FIG. 5 is a perspective view showing the main body in a state where the main body is folded.

First, the balloon mounting jig will be described. FIG. 3 is a plan view of a balloon mounting jig. FIG. 4 is a perspective view in a state where a first opening part and a second opening part of a main body are opened. FIG. 5 is a perspective view of a state where the main body is folded.

The balloon mounting jig 100 has a main body 102 that is formed in a hollow cylindrical shape having a first opening part 104 at one end thereof and a second opening part 106 at the other end thereof. The second opening part 106 of the main body 102 has a pair of guide pieces 108*a* and 108*b* that face each other with the second opening part 106 interposed therebetween. Further, the main body 102 is formed with two sets of bent parts 110*a*, 110*b*, and 110*c* that are provided from one end thereof to the other end thereof and allow the main body 102 to be bent inward in both directions. The main body 102 may be bent inward by folding the bent parts 110*a* and 110*c* in a mountain form and folding the bent part 110*b* in a valley form. In addition, the main body 102 may be folded flat by being bent at the bent parts 110*a*, 110*b*, and 110*c*, and the pair of guide pieces 108*a* and 108*b* may be superimposed as shown in FIG. 5.

The pair of guide pieces 108*a* and 108*b* are provided so as to extend from the second opening part 106 toward a distal end side opposite to the side of the first opening part 104. The width of the pair of guide pieces 108*a* and 108*b* is formed to have a width narrower than that of the main body 102 that is folded flat. Thus, in a case where the balloon mounting jig 100 is mounted to the balloon 60, it is possible to dispose the pair of guide pieces 108*a* and 108*b* inside the first sleeve part 60A and the second sleeve part 60B of the balloon 60. In a case where the insertion part 12 of the endoscope 10 is mounted to the balloon 60, the insertion part 12 is inserted along the pair of guide pieces 108*a* and 108*b*, so that the insertion part 12 can be easily inserted into the first sleeve part 60A and the second sleeve part 60B.

On the first opening part 104 of the main body 102, there is provided a wing part 112 that extends from the first opening part 104 and has a width larger than that of the main body 102 that is folded flat. The wing part 112 is formed to extend only on one side of opposite ends of the first opening part 104 in a case where the main body 102 is folded, but the wing part 112 may be formed on both sides thereof. The wing part 112 is a portion that comes into contact with a recess part when contained in the container (see FIG. 8), which will be described later, in which as the wing part 112 is in contact with the recess part, movement and rotation of the main body 102 is prevented.

It is preferable that the main body 102 and the pair of guide pieces 108*a* and 108*b* are made of a material that does not easily adhere to a rubber product such as silicone rubber or latex which is a balloon material, and specifically, paper such as drawing paper or Kent paper, or resin such as fluorine resin, silicone resin, polypropylene resin, or polycarbonate resin may be used. Further, in a case where the main body 102 and the pair of guide pieces 108*a* and 108*b* are made of paper, it is preferable that YUPO paper (registered trademark) that can easily expand and fold the main body 102 and is not easily torn.

Form of Balloon and Balloon Mounting Jig in Container

Figure 6:
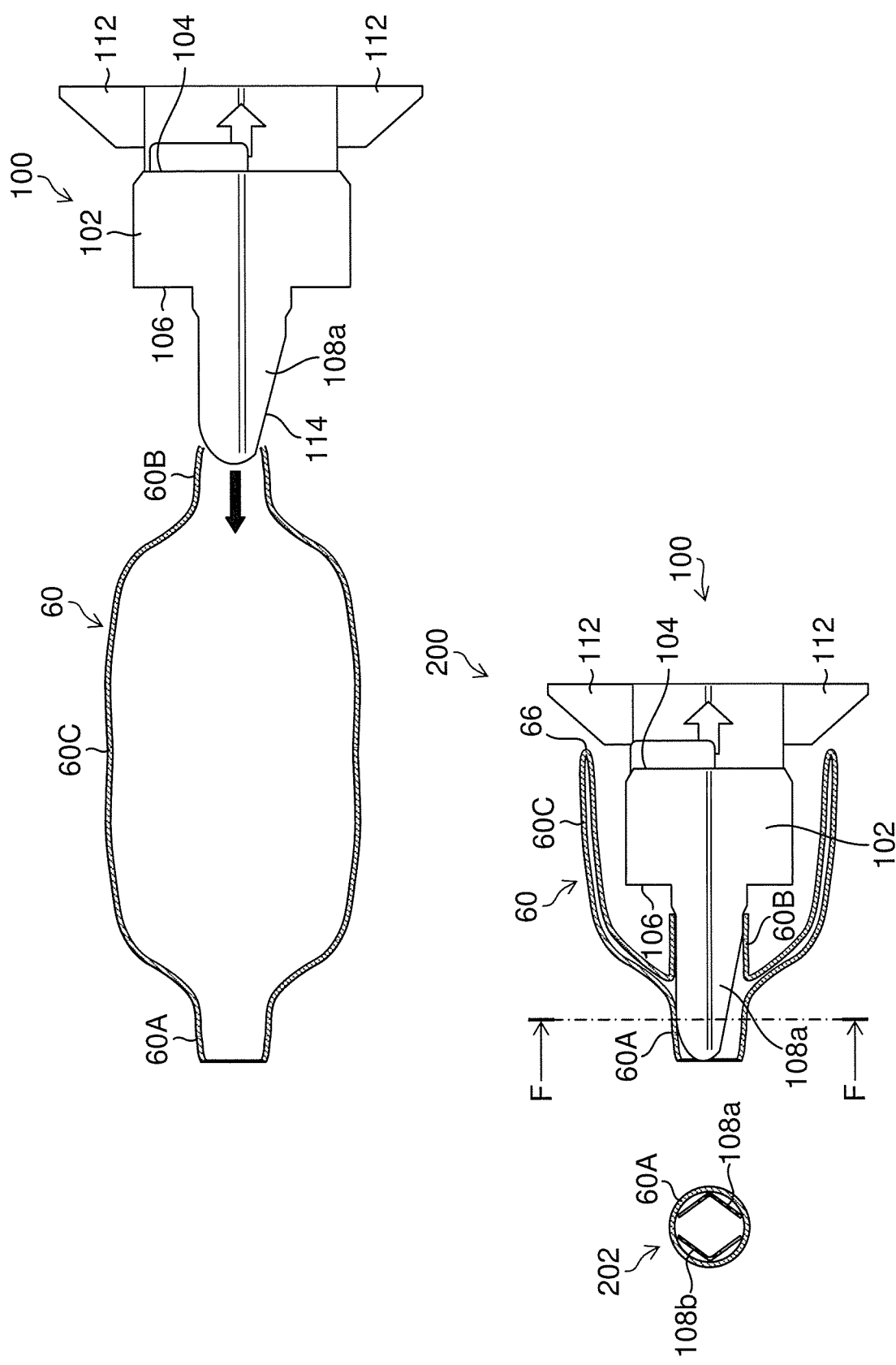
FIG. 6 is a diagram illustrating a mounting jig mounted balloon.

Next, a form in the container (which will be described later) of the balloon 60 and the balloon mounting jig 100 will be described. FIG. 6 is a diagram illustrating a mounting jig mounted balloon. A mounting jig mounted balloon 200 is configured by mounting the balloon mounting jig 100 to the balloon 60.

In a case where the balloon mounting jig 100 is mounted to the balloon 60, first, the pair of guide pieces 108*a* and 108*b* is inserted into the second sleeve part 60B, and a portion of the distal end side of the pair of guide pieces 108*a* and 108*b* is projected from the second sleeve part 60B. Further, by inserting the pair of guide pieces 108*a* and 108*b* inside the balloon main body 60C, the second sleeve part 60B moves to the first sleeve part 60A, the balloon main body 60C is folded back inside, so that a folded opening part 66 is formed. Further, by inserting the guide pieces 108*a* and 108*b* and the main body 102 from the folded opening part 66, the portion of the distal end side of the guide pieces 108*a* and 108*b* protruding from the second sleeve part 60B is inserted into the first sleeve part 60A, to thereby make it possible to mount the balloon mounting jig 100 to the balloon 60.

As shown in FIG. 6, in a state where the balloon mounting jig 100 is mounted to the balloon 60, the second sleeve part 60B is disposed inside the folded opening part 66. In the pair of guide pieces 108*a* and 108*b*, the distal end side of the guide pieces 108*a* and 108*b* is disposed inside the first sleeve part 60A. Further, a proximal end side of the guide pieces 108*a* and 108*b* is disposed inside the second sleeve part 60B. The pair of guide pieces 108*a* and 108*b* in the first sleeve part 60A is disposed to be bent outward along a longitudinal direction A (see FIG. 3) of the pair of guide pieces 108*a* and 108*b*, as shown in an F-F cross section 202. Thus, in a state where the balloon mounting jig 100 is contained, the first opening part 104 may be slightly opened from the completely folded state. Accordingly, it is possible to easily insert the insertion part 12 of the endoscope 10 into the first opening part 104.

In the container, since the balloon main body 60C is folded inward, the balloon 60 is contained in a state where inner sides of the balloon main body 60C are in contact with each other. As a method for manufacturing the balloon 60, for example, a method for immersing a mold in a resin solution that becomes a balloon material, extracting the mold from the resin solution, and drying the mold to form a balloon around the mold may be used. Then, the balloon is manufactured by extracting the mold from the inside of the balloon. Since fine irregularities are formed on an outer surface of the mold and the inside of the balloon 60 is in contact with the mold at the time of manufacturing, the fine irregularities are transferred to form a texture. Accordingly, in a case where inner surfaces of the balloon 60 are in contact with each other, even in a case where there is stickiness (tack), it is possible to maintain a stable shape without sticking. Further, since the balloon mounting jig 100 is disposed in the folded opening part 66 of the balloon 60, it is possible to prevent the surfaces of the balloon 60 from contacting and sticking to each other. Thus, it is possible to prevent sticking of the surfaces at the time of extracting balloon 60 from the container.

Container

Figure 7:
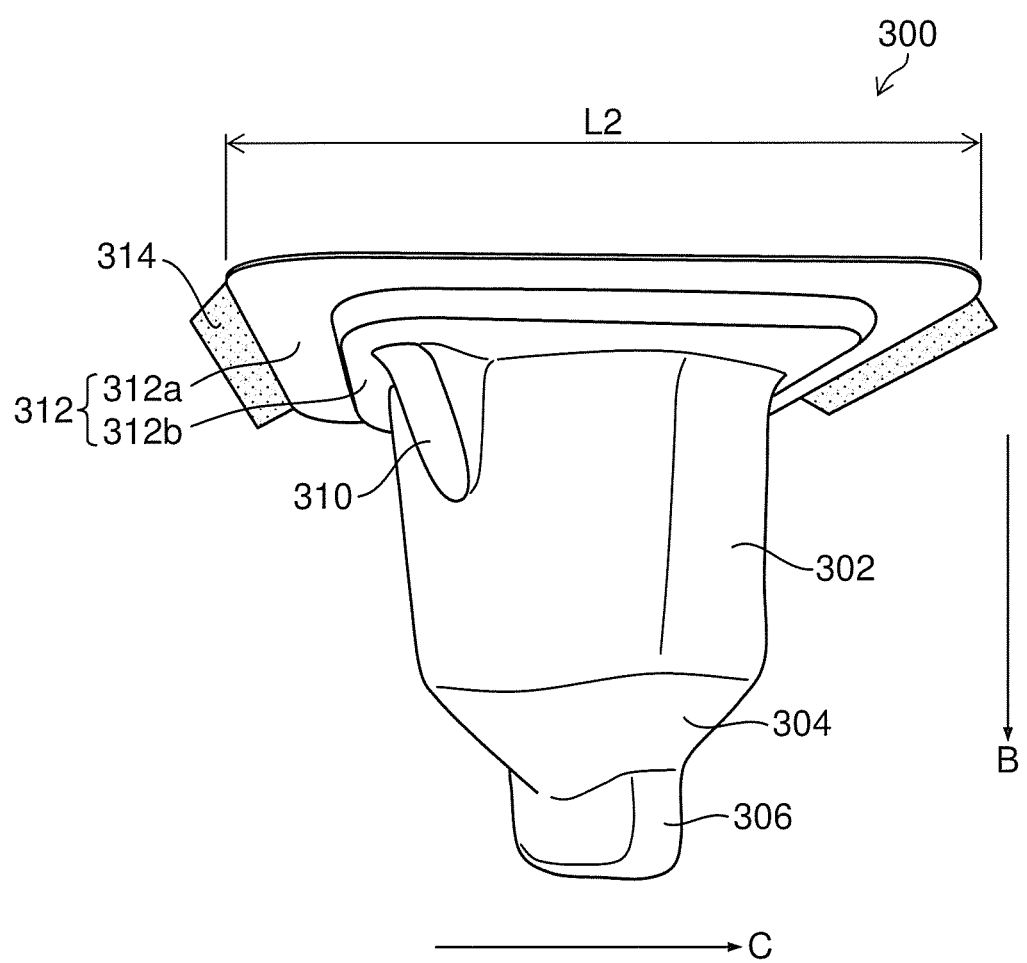
FIG. 7 is a perspective view showing a container.
Figure 8:
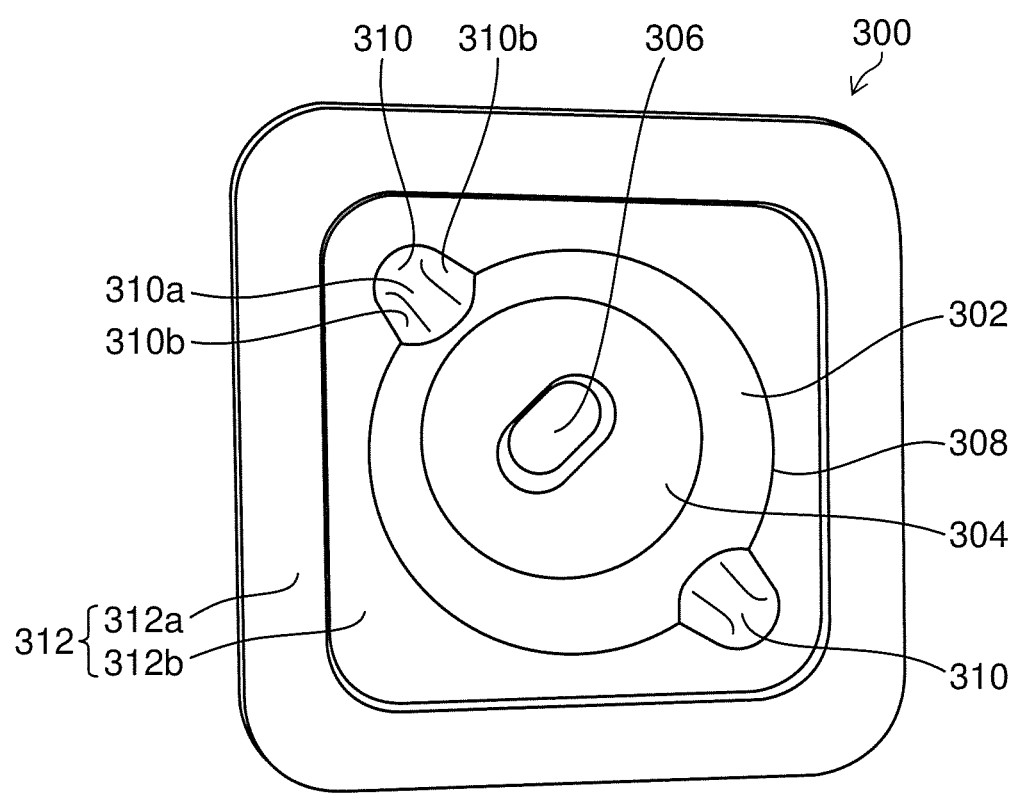
FIG. 8 is a plan view showing the container with a lid part removed.
Figure 9:
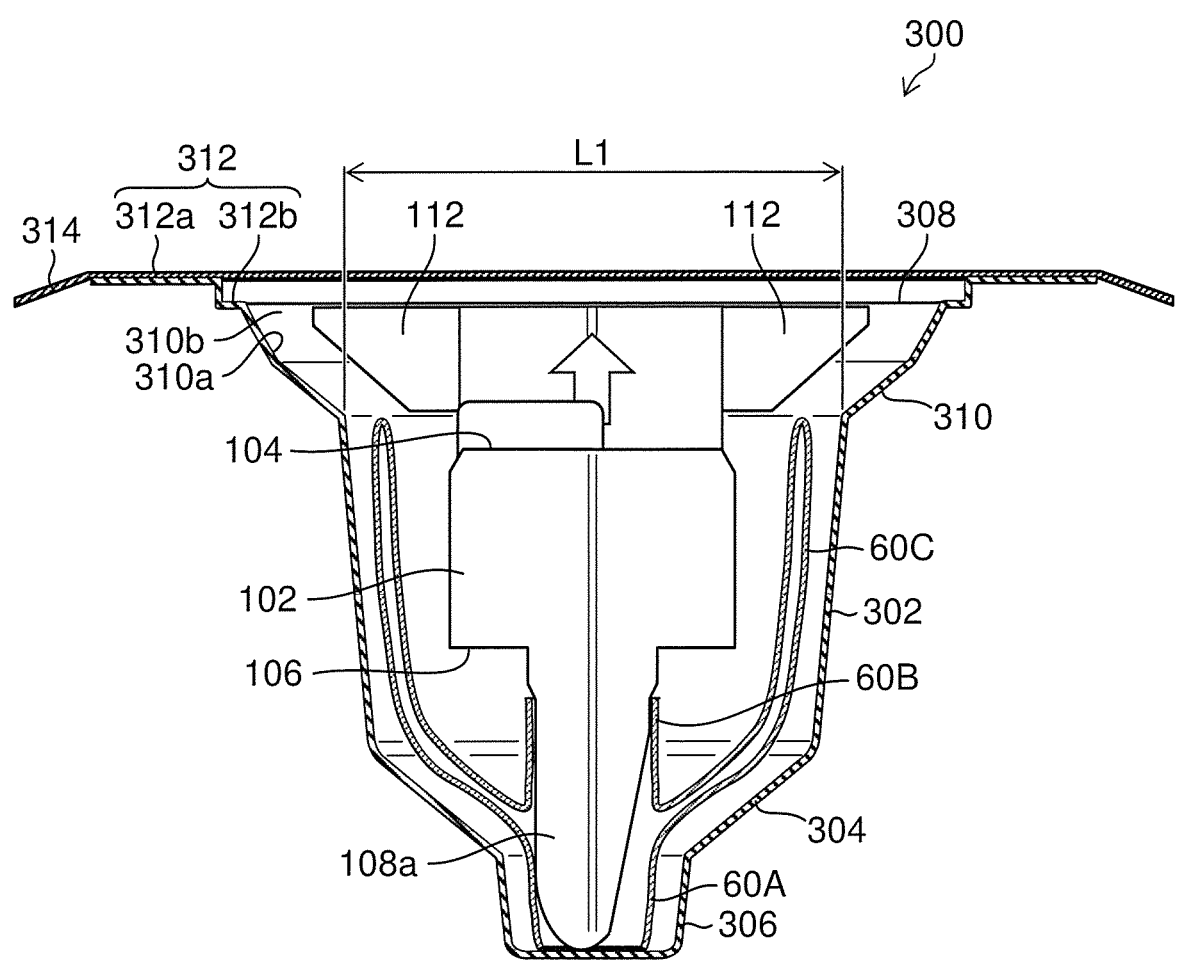
FIG. 9 is a cross-sectional view showing a state where the mounting jig mounted balloon is contained.
Figure 10:
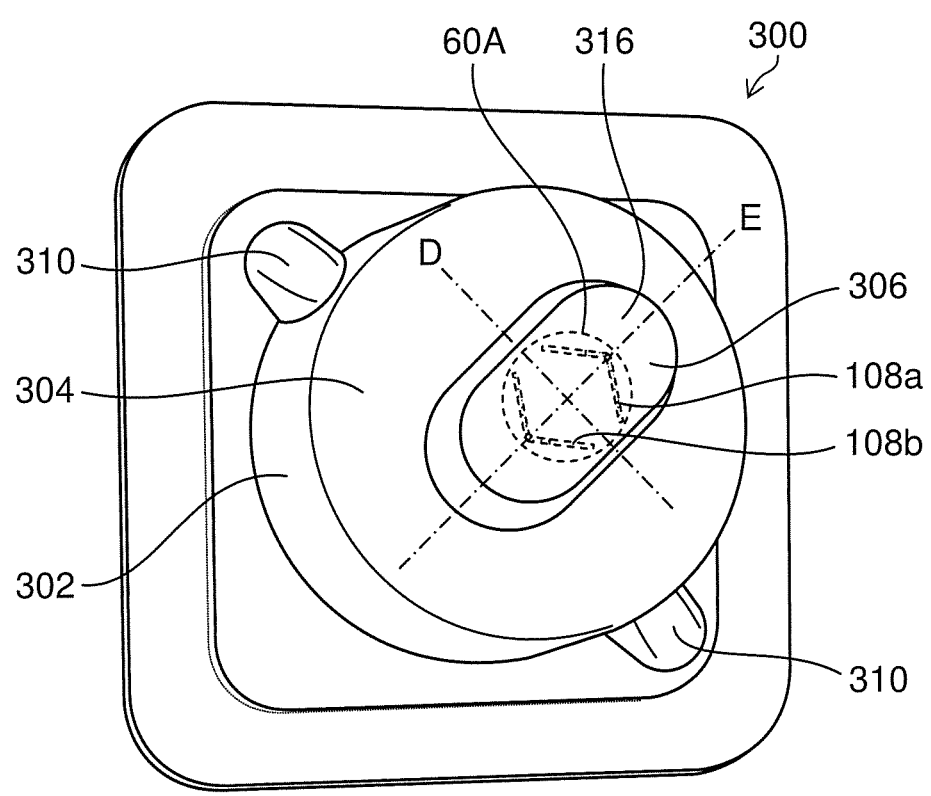
FIG. 10 is a diagram as seen from a bottom side of FIG. 9.

Next, the container that contains the mounting jig mounted balloon 200 will be described. FIG. 7 is a perspective view showing a container, and FIG. 8 is a plan view showing a state where a lid part is removed. FIG. 9 is a cross-sectional view showing a state where a mounting jig mounted balloon is contained in the container, and FIG. 10 is a diagram as seen from a bottom side of FIG. 9.

A container 300 includes a cylindrical trunk 302 having a bottom, a small groove part 306 that is provided on a bottom 304 of the trunk 302 and has an inner diameter smaller than that of the trunk 302, and an container opening part 308 that is provided opposite to the bottom 304. On the side of the container opening part 308 of the trunk 302, a recess part 310 formed in a concave shape in a direction perpendicular to an insertion direction B of the balloon mounting jig 100 is provided. Further, the container opening part 308 has a flange part 312 that extends from the container opening part 308 in a direction perpendicular to the insertion direction B of the balloon mounting jig 100, and a lid part 314 is attached to the flange part 312.

In a case where the container 300 of the mounting jig mounted balloon 200 is contained, the balloon main body 60C and the second sleeve part 60B of the balloon 60 are contained in the trunk 302, and the first sleeve part 60A is contained in the small groove part 306. By containing the balloon main body 60C in the trunk 302, it is possible to prevent sticking of the balloon main body 60C disposed around the balloon mounting jig 100, to thereby maintain the shape of the balloon main body 60C.

It is preferable that the trunk 302 is formed in a taper shape in which an inner diameter becomes larger from the bottom 304 toward the container opening part 308. By forming the taper shape that expands toward the container opening part 308, it is possible to easily take out the mounting jig mounted balloon 200. Further, even in manufacturing the container 300, it is possible to easily extract the container 300 from a mold by forming the container 300 to expand toward the container opening part 308.

It is preferable that a maximum inner diameter L1 of the trunk 302 is set to be 102% or more and 110% or less of an outer diameter of the balloon main body 60C in a natural state. By setting the inner diameter L1 of the trunk 302 within this range, it is possible to easily put the mounting jig mounted balloon 200 in the container 300. In addition, it is possible to prevent the mounting jig mounted balloon 200 from moving in the container 300. In a case where the trunk 302 is formed in the taper shape in which the inner diameter becomes larger toward the container opening part 308, the inner diameter L1 of the trunk 302 at the container opening part 308 becomes the maximum inner diameter.

The small groove part 306 contains the first sleeve part 60A and the pair of guide pieces 108a and 108b. The small groove part 306 has an elliptical sectional shape cut in a direction C perpendicular to an axis direction of the trunk 302 (the same direction as the insertion direction B of the balloon mounting jig 100). In a state where the mounting jig mounted balloon 200 is contained in the container 300, the distal end of the pair of guide pieces 108a and 108b is preferably disposed along a short axis direction D of the elliptical shape of the small groove part 306 (see FIG. 10). "The guide pieces are disposed along the short axis direction" means that the pair of guide pieces is respectively disposed on both sides centering around the short axis of the small groove part 306.

In the recess part 310, the wing part 112 of the balloon mounting jig 100 is contained. The recess part 310 has a positioning surface 310a that is formed in a direction perpendicular to the insertion direction B of the balloon mounting jig 100, and a first restricting surface 310b that is formed in a circumferential direction of the trunk. In a case where the positioning surface 310a and the wing part 112 of the balloon mounting jig 100 are in contact with each other, a position in the direction perpendicular to the insertion direction B of the balloon mounting jig 100 is determined, and thus, it is possible to prevent the balloon main body 60C from contacting the side surface of the trunk 302, to thereby stabilize the form of the balloon.

Further, similarly, the first restricting surface 310b is in contact with the wing part 112 to restrict a rotation direction with respect to a central axis in the insertion direction B of the balloon mounting jig 100. Thus, it is possible to prevent rotation of the mounting jig mounted balloon 200 due to transportation, to prevent sticking of the balloon main body 60C disposed around the balloon mounting jig 100, and to retain the form of the balloon main body 60C.

The flange part 312 is formed to expand from the container opening part 308 in a direction perpendicular to the insertion direction B of the balloon mounting jig 100. The flange part 312 is configured by an outer peripheral part 312a and an inner peripheral part 312b, and is provided in the order of the inner peripheral part 312b and the outer peripheral part 312a from the container opening part 308. The inner peripheral part 312b is formed closer to the bottom 304 than the outer peripheral part 312a in the insertion direction B of the balloon mounting jig 100. That is, the outer peripheral part 312a and the inner peripheral part 312b are formed in a stepped shape, in which the outer peripheral part 312a is formed to protrude on a side opposite to the side of the bottom 304.

The lid part 314 is attached to the flange part 312, and seals the inside of the container 300 to ensure sterility. The lid part 314 is attached to an affix target surface provided on a proximal end side of the outer peripheral part 312a of the flange part 312. By affixing the lid part 314 to the outer peripheral part 312a, it is possible to make an area where the lid part 314 is attached small.

Balloon Mounting Method

Next, a balloon mounting method will be described with reference to FIGS. 11 to 18.

Figure 11:
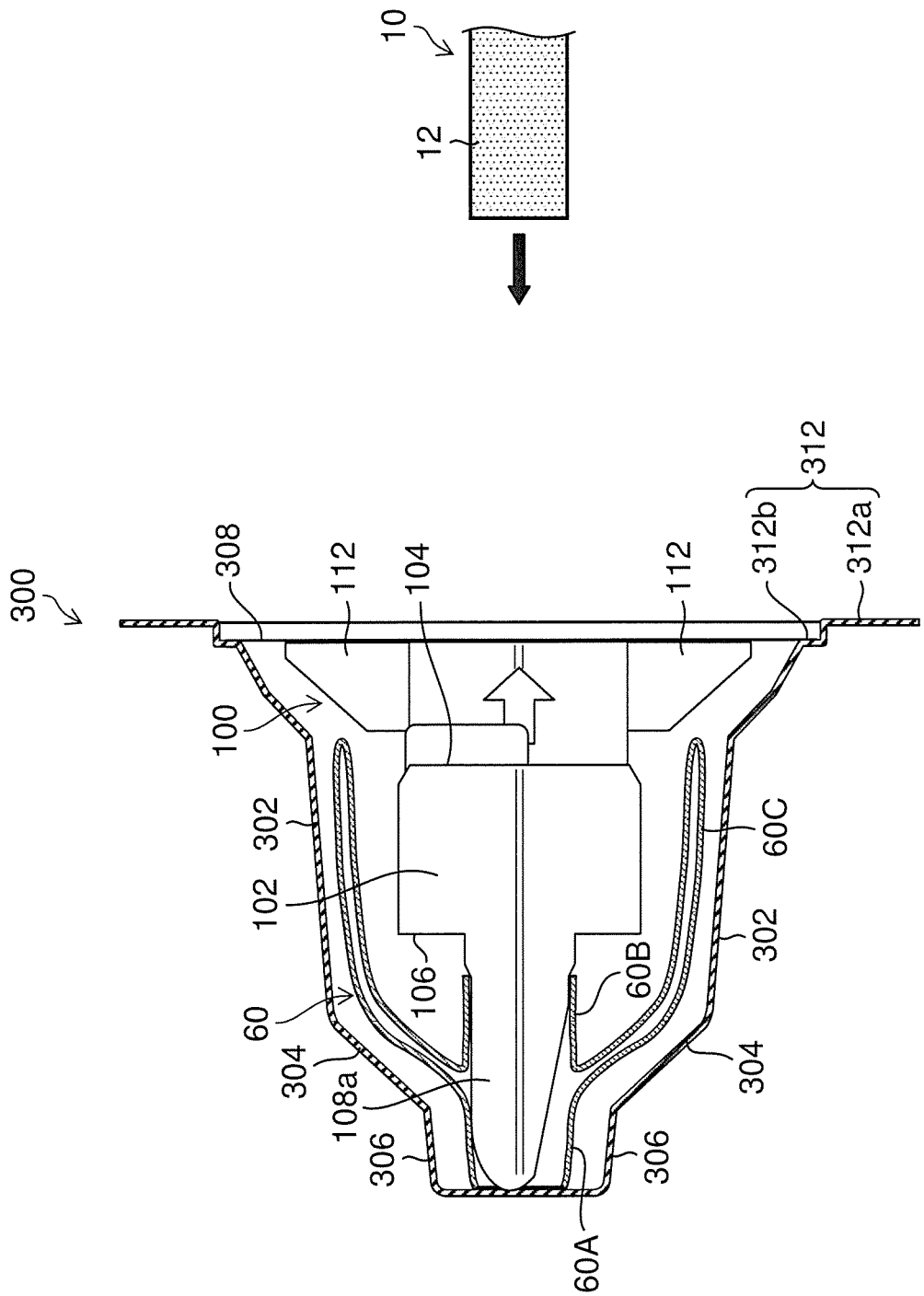
FIG. 11 is a diagram for explaining a method for mounting the balloon in the insertion part.
Figure 12:
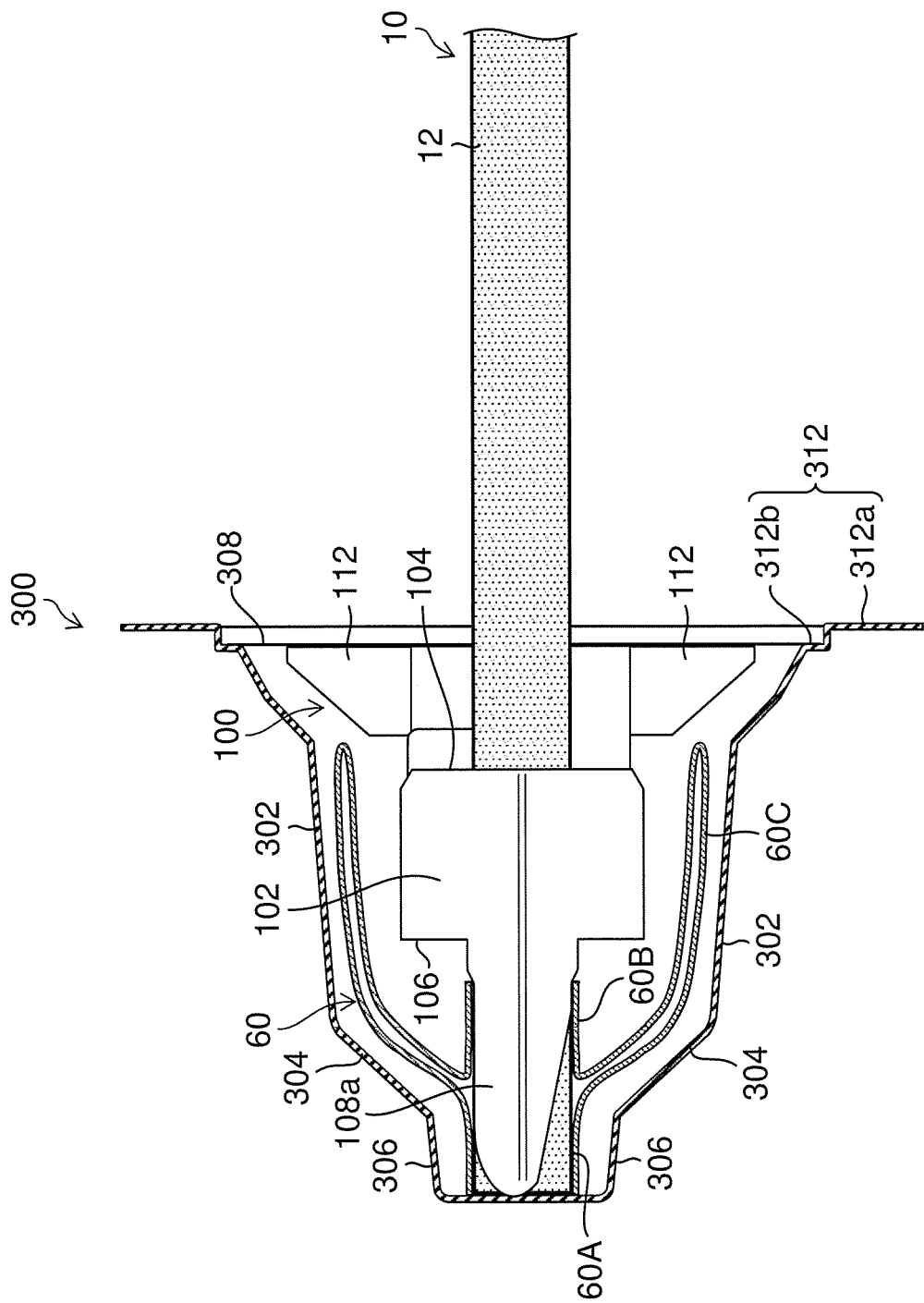
FIG. 12 is a diagram for explaining a method for mounting the balloon in the insertion part.

The package of the mounting jig mounted balloon is prepared, and the lid part 34 is removed. FIG. 11 is a diagram showing a state where the insertion part of the endoscope is inserted into the package of the mounting jig mounted balloon from which the lid part is removed. As shown in FIG. 12, the package of the mounting jig mounted balloon from which the lid part 314 is removed is disposed so that the side of the first opening part 104 of the balloon mounting jig 100 is disposed on the side of the container opening part 308 of the container 300. In this state, the insertion part 12 of the endoscope 10 is inserted from the first opening part 104. The insertion part 12 is inserted until the insertion part 12 runs into the small groove part 306 of the container 300.

FIG. 12 is a diagram for explaining a state where the insertion part is inserted until a distal end of the insertion part runs into a distal end of the small groove part. The insertion part 12 inserted from the first opening part 104 passes through the inside of the main body 102, and is inserted from the second opening part 106 between the pair of guide pieces 108a and 108b. As shown in FIG. 6, in the mounting jig mounted balloon 200, the first sleeve part 60A and the second sleeve part 60B are disposed outside the pair of guide pieces 108a and 108b. Accordingly, by inserting the insertion part 12 between the pair of guide pieces 108a and 108b, it is possible to insert the insertion part 12 into the first sleeve part 60A and the second sleeve part 60B through the pair of guide pieces 108a and 108b.

Further, as shown in FIG. 10, in a state where the mounting jig mounted balloon 200 is contained in the container 300, the distal end of the pair of guide pieces 108a and 108b is disposed along the short axis direction D of the elliptical shape of the small groove part 306. In a case where the insertion part 12 is inserted into the first sleeve part 60A through the pair of guide pieces 108a and 108b, the insertion part 12 contacts the first sleeve part 60A in the short axis direction D of the small groove part 306. Further, the insertion part 12 is pinched in the short axis direction D of the small groove part 306. In a long axis direction E of the small groove part 306, since the insertion part 12 is in contact with the pair of guide pieces 108a and 108b, it is possible to easily move the insertion part 12 compared with a case where the insertion part 12 is in contact with the first sleeve part 60A. Further, in the long axis direction E, spaces 316 are provided on opposite sides of the inserted insertion part 12 with the first sleeve part 60A being interposed therebetween. Thus, the insertion part inserted into the first sleeve part 60A is fixed in the short axis direction D of the small groove part 306, and the insertion part 12 may be moved in the long axis direction E. Accordingly, by inserting the insertion part 12 while moving the insertion part 12 in the long axis direction, it is possible to insert the insertion part 12 up to the distal end of the small groove part 306.

Further, in the mounting jig mounted balloon 200, it is preferable that the distal end of the pair of guide pieces 108a and 108b is contained in the container 300 in a state of protruding from the distal end of the first sleeve part 60A by about 0.5 to 3 mm in consideration of such a dimension that the distal end of the insertion part 12 drags the balloon in mounting the balloon to protrude from the distal end. In a state where the pair of guide pieces 108a and 108b is in contact with the distal end of the small groove part 306, as the distal end of the insertion part 12 is inserted until the insertion part 12 runs into the distal end of the small groove part 306, it is possible to make the end of the first sleeve part 60A and the distal end of the insertion part 12 match each other.

Figure 13:
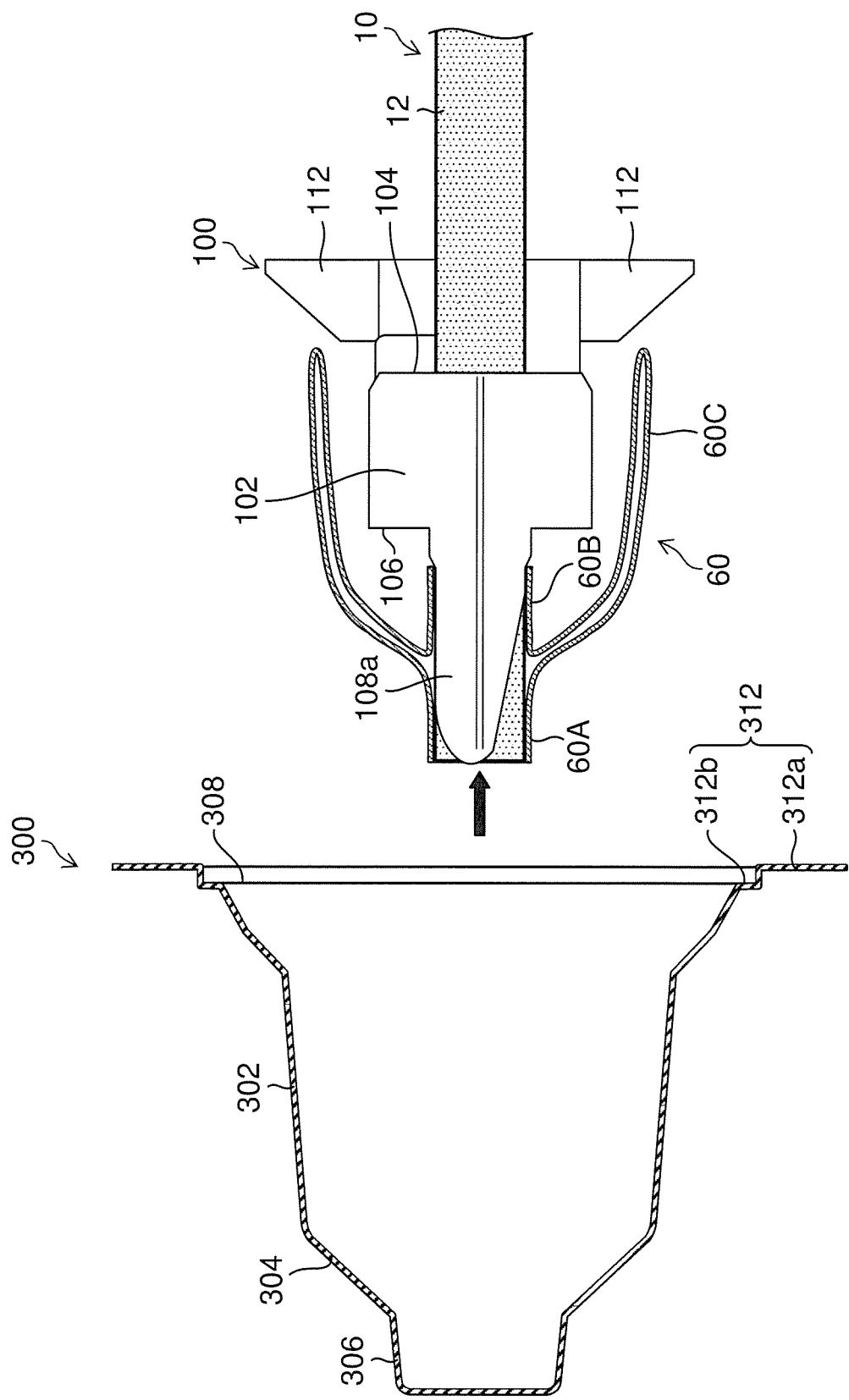
FIG. 13 is a diagram for explaining a method for mounting the balloon in the insertion part.

Next, as shown in FIG. 13, the mounting jig mounted balloon 200 into which the insertion part 12 is inserted is pulled out of the container 300. In the pulled-out mounting jig mounted balloon 200 and the endoscope 10, in a case where positions of the distal end of the insertion part 12 and the end of the first sleeve part 60A of the balloon 60 do not match each other, the balloon mounting jig 100 is moved in the longitudinal axis direction of the insertion part 12 so that the positions of the distal end of the insertion part 12 and the end of the first sleeve part 60A of the balloon 60 match each other. In pulling out the mounting jig mounted balloon 200 and the endoscope 10, and in a case where the positions of the distal end of the insertion part 12 and the end of the first sleeve part 60A of the balloon 60 match each other, this process may not be performed.

Figure 14:
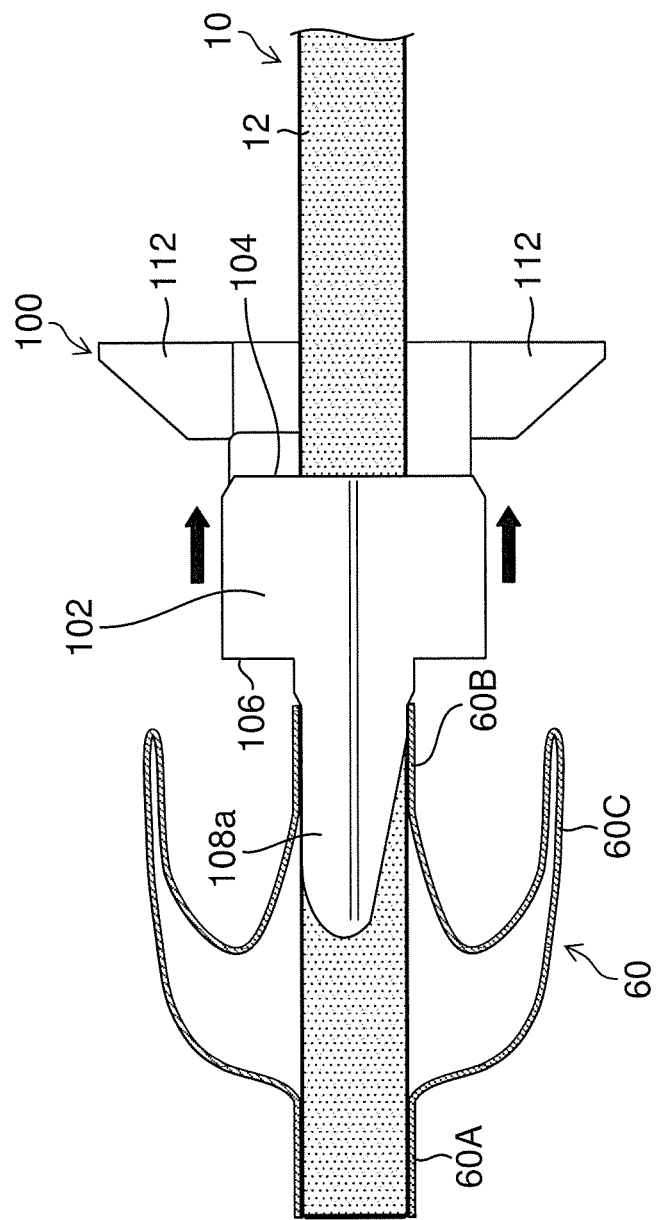
FIG. 14 is a diagram for explaining a method for mounting the balloon in the insertion part.
Figure 15:
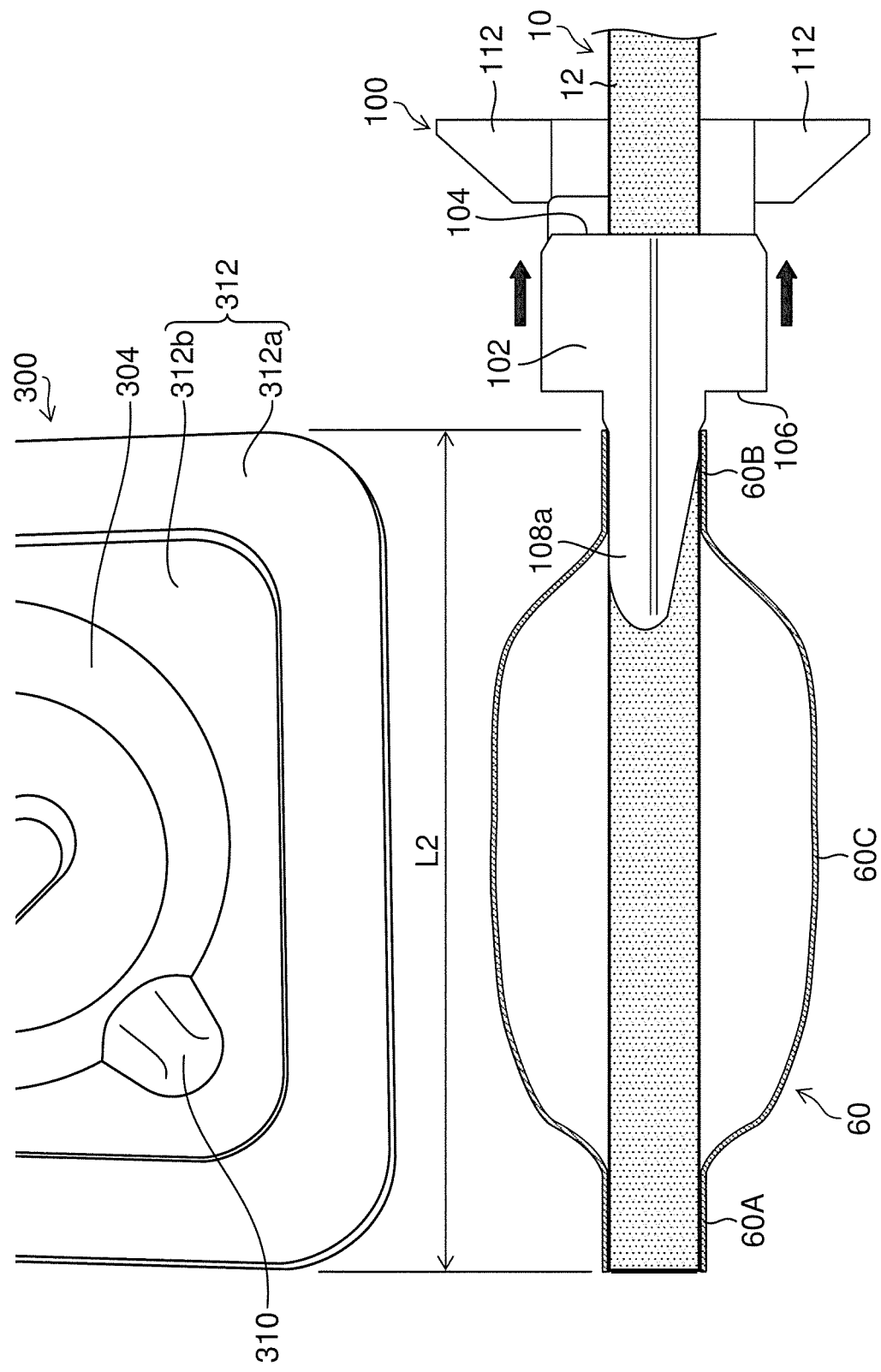
FIG. 15 is a diagram for explaining a method for mounting the balloon in the insertion part.

Next, a portion where the insertion part 12 and the first sleeve part 60A are in contact with each other is pressed. Specifically, the first sleeve part 60A is pressed against the insertion part 12 while avoiding the portion of the pair of guide pieces 108a and 108b of the insertion part 12. Further, in a state where the first sleeve part 60A is pressed, as shown in FIG. 14, the balloon mounting jig 100 is moved to the proximal end side of the insertion part 12. By moving the balloon mounting jig 100 in a state where the first sleeve part 60A is pressed, it is possible to fix the position of the first sleeve part 60A, and to move the position of the second sleeve part 60B together with the balloon mounting jig 100. Thus, as shown in FIG. 15, the second sleeve part 60B is moved out of the folded opening part 66, and the second sleeve part 60B is moved to a position that is a balloon mounting length.

Adjustment of the balloon mounting length may be performed using the flange part 312 of the container 300. A length L2 from one end of the flange part 312 to the other end thereof is set to be equal to the balloon mounting length (see FIG. 7). "The balloon mounting length" refers to a length from the end of the first sleeve part 60A to the end of the second sleeve part 60B in a state where the balloon 60 is mounted on the insertion part 12 of the endoscope 10. By setting the length L2 of the flange part 312 to be equal to the balloon mounting length, it is possible to use the balloon 60 mounted to the insertion part 12 as a guideline for adjusting the length to an appropriate length, and thus, it is possible to easily adjust the length of the balloon 60.

Figure 16:
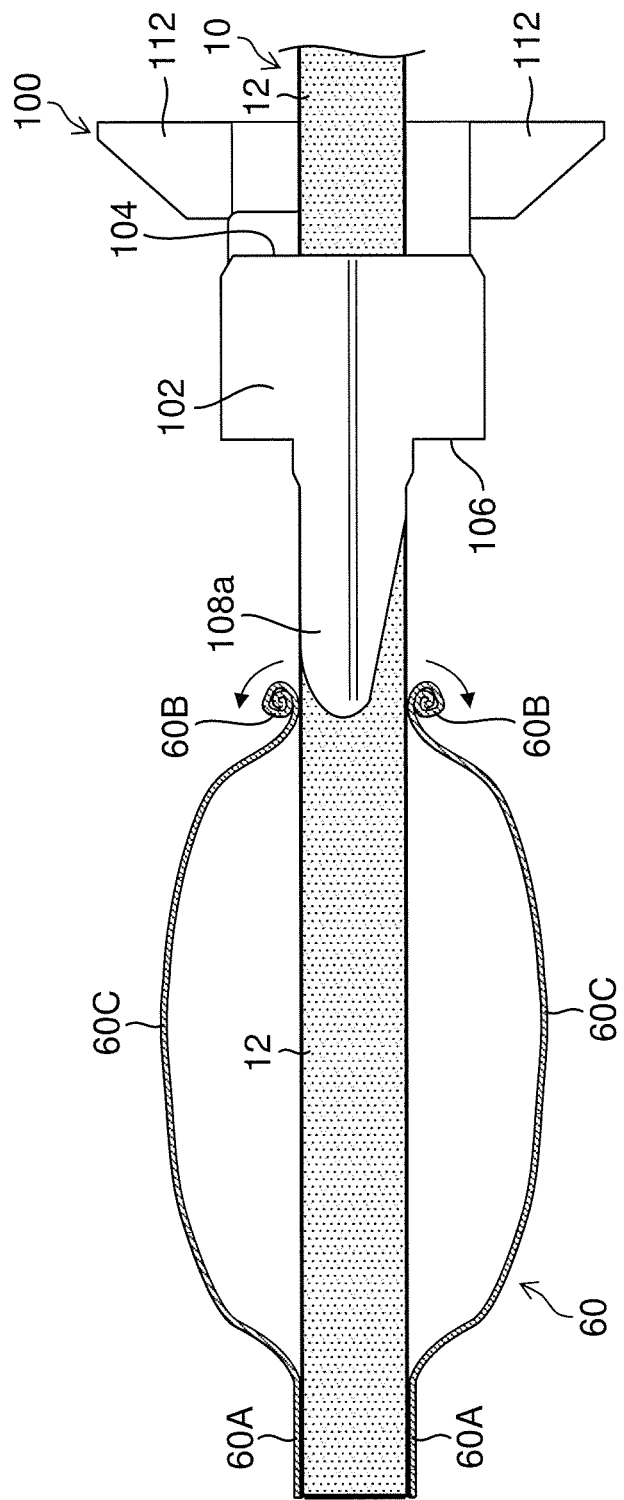
FIG. 16 is a diagram for explaining a method for mounting the balloon in the insertion part.

Next, as shown in FIG. 16, the second sleeve part 60B is wound toward the first sleeve part 60A until the pair of guide pieces 108a and 108b is removed while taking care so that the position of the balloon 60 is not moved. After winding the second sleeve part 60B until the pair of guide pieces 108a and 108b is removed, the balloon mounting jig 100 is removed. The balloon mounting jig 100 is configured to be extracted by moving the balloon mounting jig 100 toward the insertion part 12 in the distal end direction in a state where the first opening part 104 and the second opening part 106 of the main body 102 are opened. In a case where the balloon mounting jig 100 is formed of paper, the balloon mounting jig 100 may be broken and removed.

Figure 17:
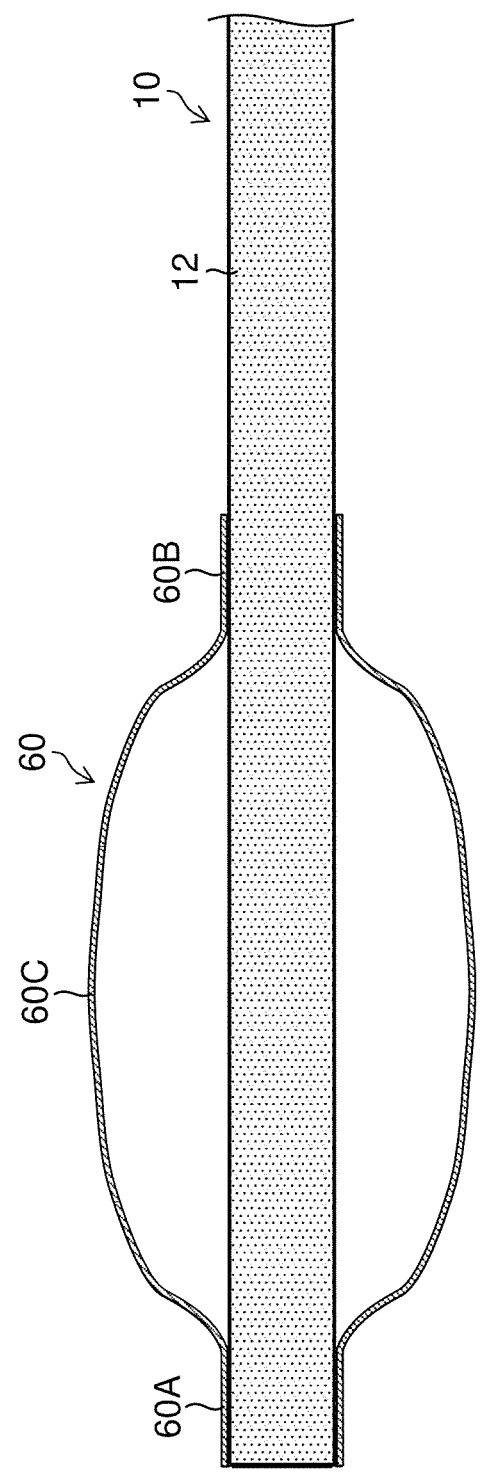
FIG. 17 is a diagram for explaining a method for mounting the balloon in the insertion part.
Figure 18:
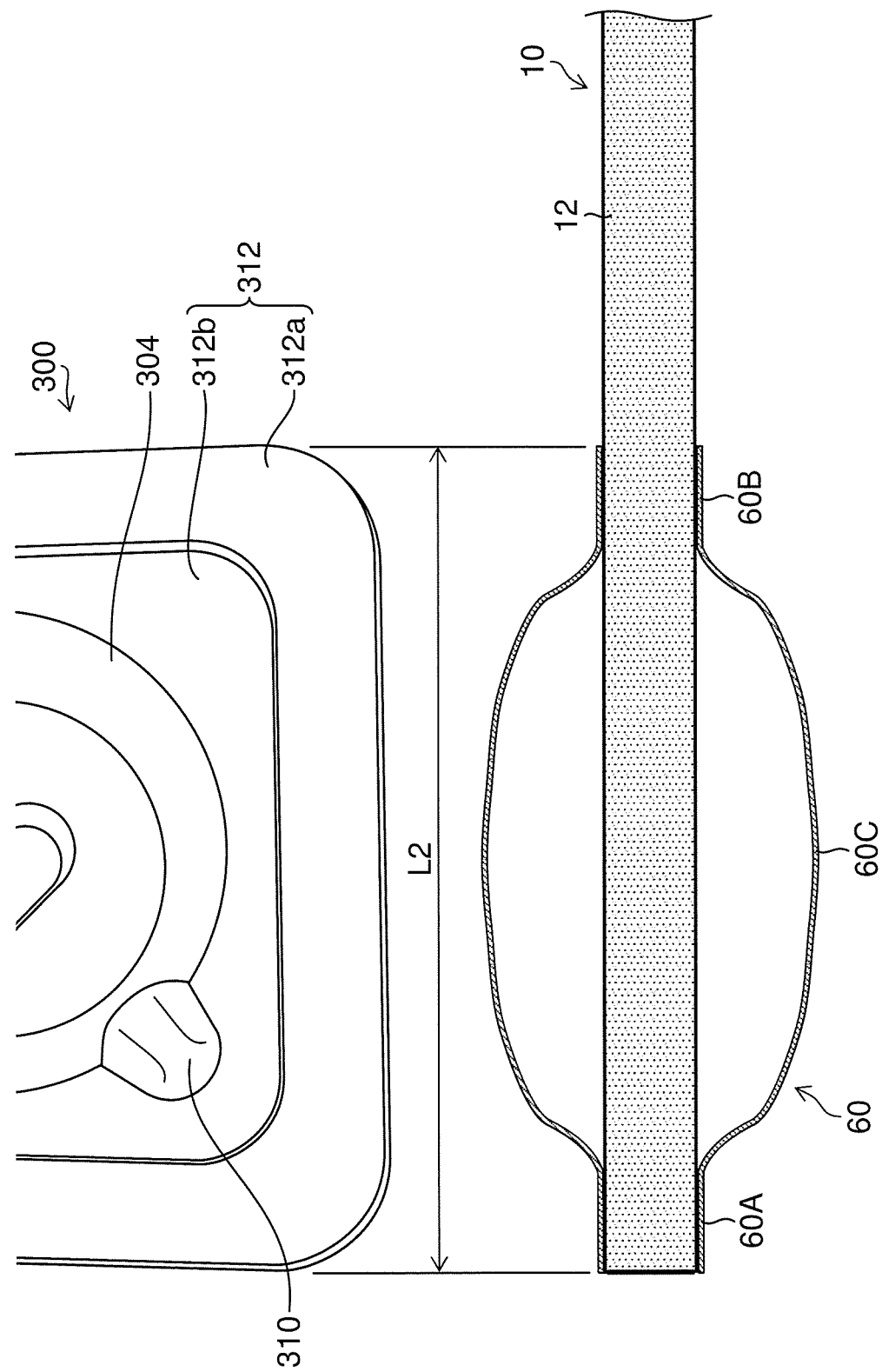
FIG. 18 is a diagram for explaining a method for mounting the balloon in the insertion part.

After removing the balloon mounting jig 100, the position of the balloon 60 is fixed so as not to move, and the second sleeve part 60B is rewound (FIG. 17). Next, as shown in FIG. 18, using the flange part 312 of the container 300, finally, the position of the second sleeve part 60B is adjusted to reach the balloon mounting length, and the balloon 60 is mounted to the insertion part 12.

Finally, the balloon 60 is fixed to the insertion part 12 by fitting the first balloon fixing member 61 and the second balloon fixing member 62 into the first sleeve part 60A and the second sleeve part 60B of the balloon 60 (see FIG. 2). As the first balloon fixing member 61 and the second balloon fixing member 62, rubber bands may be used. The mounting of the rubber bands may be performed using an apparatus disclosed in JP2013-126526A, for example. Further, a yarn may be used as the first balloon fixing member 61 and the second balloon fixing member 62, and in this case, the balloon 60 may be fixed into the insertion part 12 by winding the first sleeve part 60A and the second sleeve part 60B with the yarn.

Modified Embodiment of Container

Figure 19:
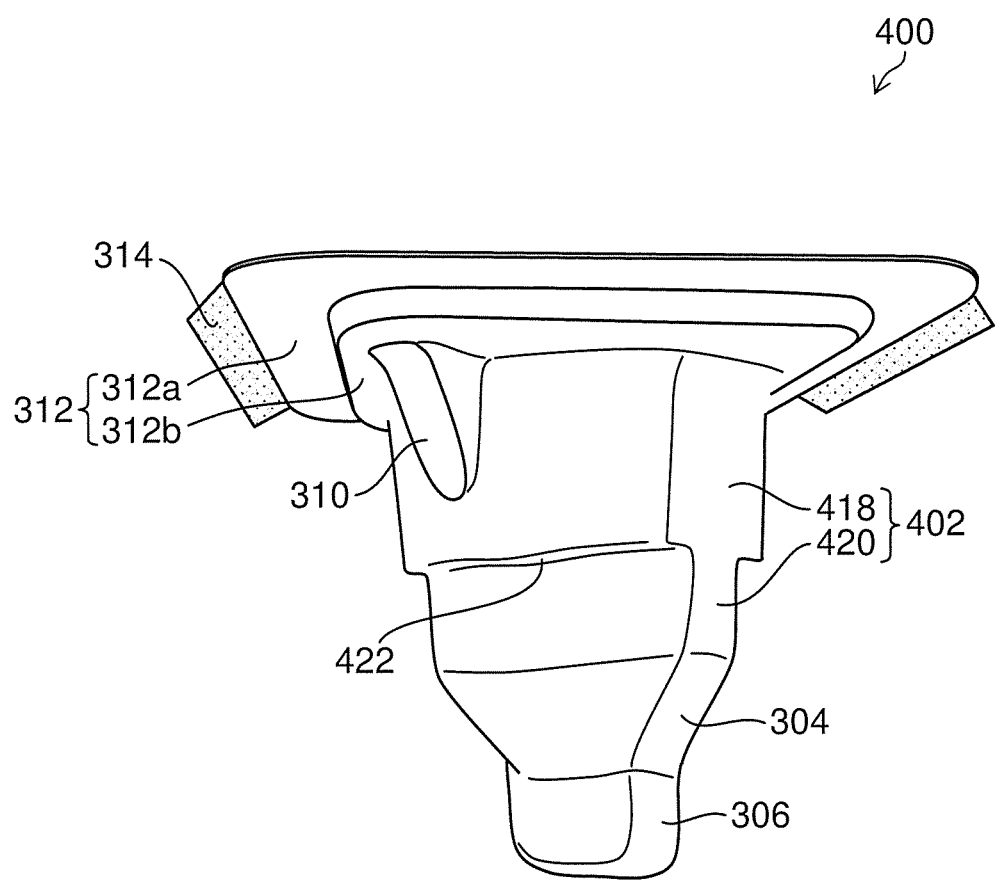
FIG. 19 is a perspective view showing a container of a modified embodiment.
Figure 20:
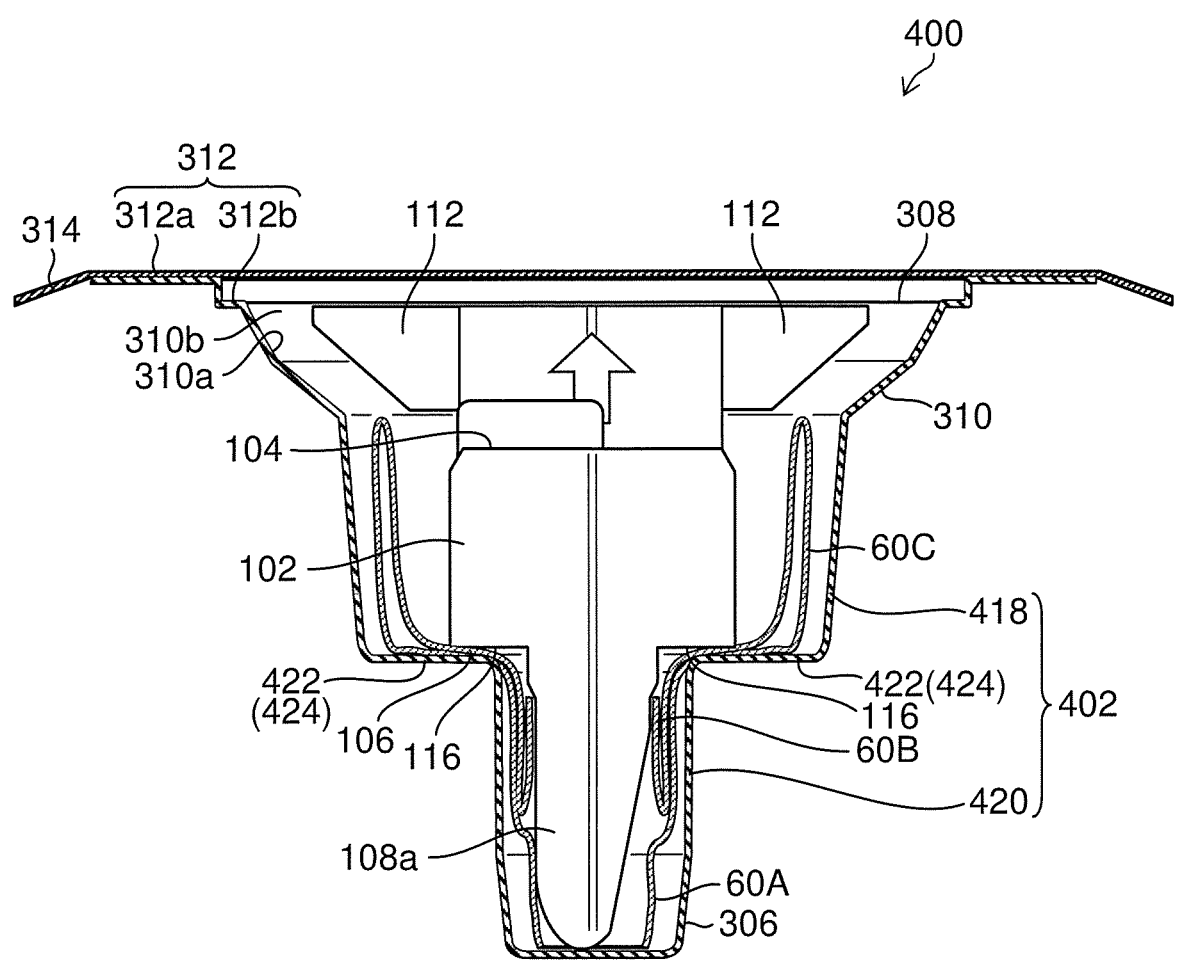
FIG. 20 is a cross-sectional view showing a state where the mounting jig mounted balloon is contained in the container of the modified embodiment.

FIG. 19 is a perspective view showing a modified embodiment of a container, and FIG. 20 is a cross-sectional view showing a state where a mounting jig mounted balloon is contained in the container.

A trunk 402 of a container 400 of the modified embodiment has a trunk main body 418 that is provided on the side of the container opening part 308, a middle groove part 420 that is provided on the side of the small groove part 306 and has a width narrower than that of the trunk main body 418, and a step part 422 that is provided between the trunk main body 418 and the middle groove part 420. In the container 400 shown in FIG. 19, the step part 422 is formed with a surface in the perpendicular direction with respect to the insertion direction of the insertion part 12.

In the container 400, the main body 102 of the balloon mounting jig 100 is contained in the trunk main body 418. The pair of guide pieces 108a and 108b of the balloon mounting jig are contained in the small groove part 306 and the middle groove part 420. By such a configuration, in a state where the balloon mounting jig 100 is contained, the end of the main body 102 of the balloon mounting jig 100 on the side of the pair of guide pieces 108a and 108b can be disposed at the boundary between the trunk main body 418 and the middle groove part 420. That is, the step part 422 that is provided between the trunk main body 418 and the middle groove part 420 of the container 400, and the end of the main body 102 of the balloon mounting jig 100 on the side of the pair of guide pieces 108a and 108b can be flush with each other in the perpendicular direction to the insertion direction of the insertion part 12 of the endoscope 10. By this configuration, the step part 422 becomes a second restricting surface 424 that restricts a position of the insertion direction of the main body 102 of the balloon mounting jig 100, and it is possible to restrict the position of the insertion direction of the balloon mounting jig 100 by the second restricting surface 424 being in contact with a restriction target part 116 that is the end of the main body 102 of the balloon mounting jig 100 on the side of the pair of guide pieces 108a and 108b.

The main body 102 of the balloon mounting jig 100 is provided with the bent parts 110a, 110b, and 110c on the side part in the width direction as shown in FIGS. 3 to 5, and the main body 102 may be folded flat by being bent inward. Since the bent parts 110a, 110b, and 110c are formed along the insertion direction of the insertion part 12 of the endoscope 10, it is possible to increase buckling strength in a case where a force is applied in the insertion direction. In a state where the balloon mounting jig 100 is contained, the position of the second restricting surface 424 is provided in the width direction of the pair of guide pieces 108a and 108b. By being in contact with the second restricting surface 424 at the positions of the bent parts 110a, 110b, and 110c of the main body 102, it is possible to prevent the main body 102 from buckling in the insertion direction. Accordingly, at the time of insertion of the insertion part 12, it is possible to prevent a force from being applied to the pair of guide pieces 108a and 108b, and to prevent the pair of guide pieces 108a and 108b from being bent. Thus, it is possible to stably insert the insertion part 12 up to the distal ends of the first sleeve part 60A of the balloon 60 and the pair of guide pieces 108a and 108b.

Further, it is possible to prevent the pair of guide pieces 108a and 108b from being bent, and thus it is possible to make buckling strength of the pair of guide pieces 108a and 108b smaller than that of the main body 102. Thus, it is possible to reduce the thickness of the pair of guide pieces 108a and 108b. By reducing the thickness of the pair of guide pieces 108a and 108b, it is possible to reduce the influence of the tension of the balloon 60 which the balloon mounting jig 100 undergoes, and since the balloon mounting jig 100 and the balloon 60 are easily moved together on the insertion part 12, it is possible to easily perform an operation of mounting a balloon, not just a case where the balloon mounting jig 100 is pulled out from the balloon 60.

Figure 21:
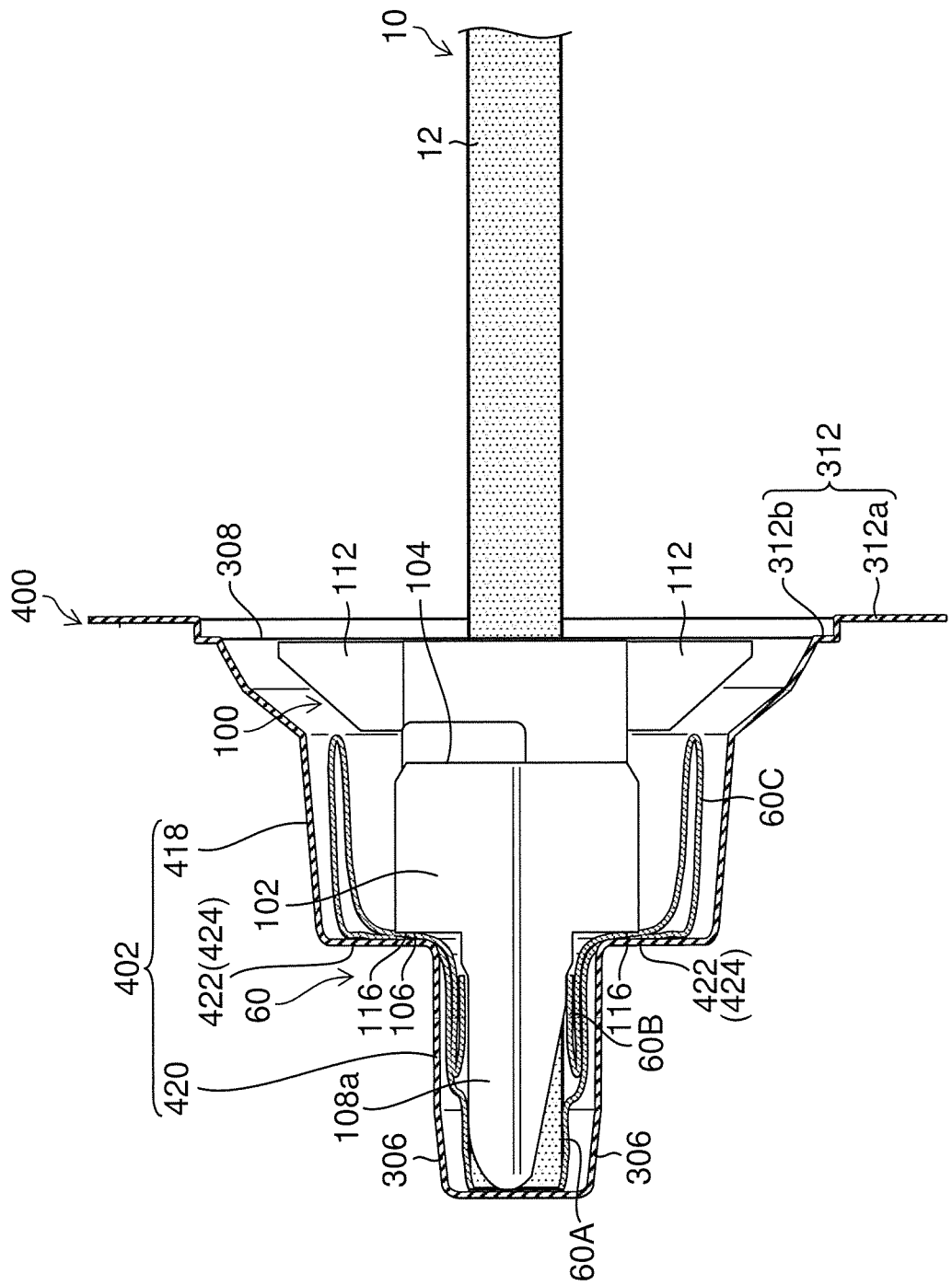
FIG. 21 is a diagram showing a state where the insertion part is inserted into the balloon mounting jig contained in the container of the modified embodiment.

FIG. 21 is a diagram showing a state where the insertion part is inserted into the balloon mounting jig contained in the container of the modified embodiment. In a case where the insertion part 12 of the endoscope 10 is inserted from the first opening part 104 of the balloon mounting jig 100 along the pair of guide pieces 108a and 108b, an insertion resistance is applied due to the influences of the tensions of the first sleeve part 60A and the second sleeve part 60B of the balloon 60, and a force is applied to the balloon mounting jig 100 in the insertion direction of the insertion part 12. In the container 400, by the step part 422 and the restriction target part 116 of the balloon mounting jig 100 being in contact with each other, it is possible to prevent the balloon mounting jig 100 from moving in the insertion direction of the insertion part 12. Accordingly, it is possible to prevent a force from being applied to the pair of guide pieces 108a and 108b in the insertion direction of the insertion part 12, and to prevent the pair of guide pieces 108a and 108b from being bent. Thus, it is possible to easily insert the insertion part 12 up to the distal end of the first sleeve part 60A of the balloon 60.

Shape of One Pair of Guide Pieces

Next, a preferable shape of the pair of guide pieces 108a and 108b will be described. As shown in FIG. 3, the pair of guide pieces 108a and 108b has a distal end part provided on the distal end side of the guide pieces 108a and 108b, and one end of the guide pieces 108a and 108b in a width direction has an inclined part 114 that is formed to be inclined with respect to the longitudinal direction A. The inclined part 114 has a linear shape toward the distal end side, and is formed so that the width of the guide pieces 108a and 108b is formed to be narrowed. Thus, the guide pieces 108a and 108b can be easily inserted into the first sleeve part 60A and the second sleeve part 60B of the balloon 60. By providing the inclined part 114, it is possible to widen the area where the insertion part 12 and the first sleeve part 60A are in contact with each other in a case where the insertion part 12 is inserted into the first sleeve part 60A through the pair of guide pieces 108a and 108b. Thus, it is possible to easily pull out the balloon mounting jig 100 from the first sleeve part 60A by pressing the area where the insertion part 12 and the first sleeve part 60A are in contact with each other with a finger.

The inclined part 114 is provided on each of the pair of guide pieces 108a and 108b. The positions of the inclined parts 114 are symmetrically provided with reference to the central axis of the main body 102. That is, in a case where the pair of guide pieces 108a and 108b is viewed from any one side of the guide pieces 108a and 108b, the inclined parts 114 are provided at positions where the inclined parts 114 do not overlap each other. By making the positions symmetrical with reference to the central axis of the main body 102, it is possible to press the first sleeve part 60A from both sides of the insertion part 12 in the width direction, to thereby easily pull out the balloon mounting jig 100.

Further, providing the inclined parts 114, it is possible to reduce a contact area between the pair of guide pieces 108a and 108b and the first sleeve part 60A. By reducing the contact area between the pair of guide pieces 108a and 108b and the first sleeve part 60A, in inserting the insertion part 12, an area where the insertion part 12 comes into contact with the first sleeve part 60A and the second sleeve part 60B becomes large. Accordingly, it is difficult to perform insertion of the insertion part 12. On the other hand, in pulling out the guide pieces 108a and 108b, it is possible to press the first sleeve part 60A to the insertion part 12, and thus, it is possible to easily pull out the guide pieces 108a and 108b.

Conversely, in a case where the contact area between the pair of guide pieces 108a and 108b and the first sleeve part 60A is large when the insertion part 12 of the endoscope 10 is inserted, it is possible to insert the insertion part 12 between the guide pieces 108a and 108b, and thus, it is possible to easily perform the insertion of the insertion part 12. However, in pulling out the guide pieces 108a and 108b from the first sleeve part 60A, since an area where the first sleeve part 60A and the insertion part 12 are pressed becomes small, it is difficult to pull out the guide pieces 108a and 108b.

In order to achieve both of easy insertion of the insertion part 12 and easy pulling out of the pair of guide pieces 108a and 108b, it is preferable that the pair of guide pieces 108a and 108b has a contact surface that has a contact area of 55% or more and 70% or less with respect to the insertion part 12 in a case where the insertion part 12 is inserted. Hereinafter, there is a table showing that in a case where the area of the pair of guide pieces 108a and 108b is changed, the ease of insertion of the insertion part 12 and the ease of pulling out of the balloon mounting jig 100 with respect to the contact area between the insertion part 12 and the pair of guide pieces 108a and 108b are compared. Evaluation was performed on the following criteria.

Ease of Insertion

A: Insertion is possible without any problem.

B: Insertion is possible, but it is necessary to strongly press the endoscope.

C: Insertion is possible, but there is a case where a distal end position of the balloon shifts.

Ease of Pulling Out

A: Pulling out is possible without any problem.

B: Pulling out is possible, but it is necessary to strongly press the balloon.

C: Pulling out is possible, but there is a case where the distal end position of the balloon shifts.

TABLE 1

| Contact area (%) | Ease of insertion | Ease of pulling out |
|---|---|---|
| 80 | A | C |
| 75 | A | C |
| 70 | A | B |
| 65 | A | A |
| 60 | B | A |
| 55 | B | A |
| 50 | C | A |
| 45 | C | A |
| 40 | C | A |

As shown in Table 1, by setting the contact area to 55% or more and 70% or less, it is possible to use both the ease of insertion of the insertion part 12 and the ease of pulling out of the guide pieces 108a and 108b.

As described above, according to the present embodiment, by inserting the insertion part 12 of the endoscope 10 from the first opening part 104 of the balloon mounting jig 100, it is possible to insert the insertion part 12 into the first sleeve part 60A and the second sleeve part 60B through the pair of guide pieces 108a and 108b. Then, by extracting the balloon 60, the balloon mounting jig 100, and the endoscope 10 from the container 300, moving the second sleeve part 60B together with the balloon mounting jig 100, and adjusting the position of the balloon 60 mounted to the endoscope 10, it is possible to easily mount the balloon 60 in the endoscope 10.

EXPLANATION OF REFERENCES

10: endoscope
12: insertion part
14: operation part
16: universal cord
18: LG connector
20: light source device
22: cable
24: electric connector
26: processor
28: air/water supply button
30: suction button
32: shutter button
34: function switching button
36: angle knob
38: balloon air supply port
40: flexible part
42: bending part
44: distal end part
46: forceps insertion part
48: air/water supply connector
49: suction connector
50: monitor
52: observation window
54: illumination window
56: air/water supply nozzle
58: forceps port
60: balloon
60A: first sleeve part
60B: second sleeve part
60C: balloon main body
61: first balloon fixing member
62: second balloon fixing member
64: ventilation hole
66: folded opening part
70: balloon control device
72: device main body
74: hand switch
76: pressure display unit
80: tube
82: backflow prevention unit
84: cord
86: balloon dedicated monitor
100: balloon mounting jig
102: main body
104: first opening part
106: second opening part
108a, 108b: guide piece
110a, 110b, 110c: bent part
112: wing part
114: inclined part
116: restriction target part
200: mounting jig mounted balloon
202: cross section
300, 400: container
302, 402: trunk
304: bottom
306: small groove part
308: container opening part 310: recess part
312: flange part
312a: outer peripheral part
312b: inner peripheral part
314: lid part
316: space
418: trunk main body
420: middle groove part
422: step part
424: second restricting surface
SW1: power switch
SW2: stop switch

What is claimed is:

1. A package of a mounting jig mounted balloon comprising:
   a balloon;
   a balloon mounting jig for mounting the balloon in an insertion part of an endoscope;
   a container for containing the balloon and the balloon mounting jig,
   wherein the balloon includes a first sleeve part provided at one end thereof, a second sleeve part provided at the other end thereof, and a balloon main body provided between the first sleeve part and the second sleeve part,
   wherein the balloon mounting jig includes a main body that is formed in a hollow cylindrical shape to be folded flat and has a first opening part at one end thereof and a second opening part at the other end thereof, and a pair of guide pieces that faces each other and is provided so as to extend from the second opening part toward a side opposite to a side where the first opening part is provided, and
   wherein inside the container, the balloon is disposed so that the balloon main body is folded inwardly and the second sleeve part is disposed inside a folded opening part formed in a folded portion of the balloon, and the balloon mounting jig is disposed so that the pair of guide pieces and at least a part of the main body are inserted from the folded opening part and the pair of guide pieces is disposed inside the first sleeve part and the second sleeve part.

2. The package of the mounting jig mounted balloon according to claim 1,
   wherein each of the pair of guide pieces has a distal end part provided on a distal end side opposite to the side where the first opening part is provided, and the distal end part has an inclined part that is formed to be inclined with respect to a longitudinal direction of the pair of guide pieces in a linear shape so that a width of each of the pair of guide pieces is narrowed toward the distal end side, and
   wherein positions of the respective inclined parts of the pair of guide pieces are provided symmetrically with respect to a central axis of the main body.

3. The package of the mounting jig mounted balloon according to claim 1,
   wherein the pair of guide pieces has a contact surface which has a contact area of 55% or more to 70% or less with respect to the insertion part of the endoscope in a case where the insertion part of the endoscope is inserted.

4. The package of the mounting jig mounted balloon according to claim 1,
   wherein materials of the main body and the pair of guide pieces are drawing paper, Kent paper, fluorine resin, silicone resin, polypropylene resin, or polycarbonate resin.

5. The package of the mounting jig mounted balloon according to claim 1,
   wherein the container has a cylindrical trunk with a bottom, a small groove part that is provided at the bottom of the trunk and has an inner diameter smaller than an inner diameter of the trunk, and a container opening part that is provided on a side opposite to the bottom,
   wherein the trunk contains the balloon main body and the second sleeve part, and
   wherein the small groove part contains the first sleeve part.

6. The package of the mounting jig mounted balloon according to claim 5,
   wherein the trunk is formed in a taper shape in which an inner diameter becomes larger from the bottom toward the container opening part.

7. The package of the mounting jig mounted balloon according to claim 5,
   wherein a cross section of the small groove part cut in a direction perpendicular to an axis direction of the trunk is elliptical, and the pair of guide pieces is disposed along a short axis direction of the elliptical shape.

8. The package of the mounting jig mounted balloon according to claim 5,
   wherein the inner diameter of the trunk is 102% or more and 110% or less of an outer diameter of the balloon main body in a where no external force is applied to the balloon.

9. The package of the mounting jig mounted balloon according to claim 5,
   wherein the balloon mounting jig has a wing part that extends from the first opening part of the main body and has a width larger than that of the main body that is folded flat,
   wherein the trunk has a recess part that is formed in a concave shape in a direction perpendicular to an insertion direction of the balloon mounting jig and contains the wing part, and
   wherein the recess part has a positioning surface that determines a position of the balloon mounting jig contained in the container in the direction perpendicular to the insertion direction of the balloon mounting jig, and a restricting surface that restricts a rotation direction of the balloon mounting jig with respect to a central axis of the balloon mounting jig in the insertion direction.

10. The package of the mounting jig mounted balloon according to claim 5,
    wherein the trunk has a trunk main body that is provided on a side of the container opening part, a middle groove part that is provided on a side of the small groove part and has a width narrower than that of the trunk main body, and a step part that is provided between the trunk main body and the middle groove part, and
    wherein the step part has a second restricting surface that restricts a position of an insertion direction of the balloon mounting jig contained in the container.

11. The package of the mounting jig mounted balloon according to claim 10,
    wherein the balloon mounting jig has a restriction target part on a side of the pair of guide pieces of the main body, and
    wherein the position of the insertion direction of the balloon mounting jig is restricted by the second restricting surface being in contact with the restriction target part.

12. The package of the mounting jig mounted balloon according to claim 10,
wherein the main body has a bent part to be folded on a side part in a width direction, and
wherein in a case where a force is applied in an insertion direction of the insertion part of the endoscope, buckling strength of the main body is larger than that of the pair of guide pieces.

13. The package of the mounting jig mounted balloon according to claim 5,
wherein in a case where a length from an end of the first sleeve part to an end of the second sleeve part in a state where the balloon is mounted on the insertion part of the endoscope is set as a balloon mounting length, the container opening part has a flange part, and a length of the flange part is equal to the balloon mounting length.

14. The package of the mounting jig mounted balloon according to claim 13,
wherein a lid part attached to the flange part is provided,
wherein the flange part is configured by an outer peripheral part and an inner peripheral part that expand from the container opening part in a direction perpendicular to the insertion direction of the balloon mounting jig, in which the inner peripheral part is formed to be closer to the bottom than the outer peripheral part inside the outer peripheral part, and
wherein the lid part is attached to the outer peripheral part.

15. A balloon mounting method using the package of the mounting jig mounted balloon according to claim 1, the method comprising:
inserting the insertion part of the endoscope into the main body from the first opening part;
inserting the insertion part of the endoscope between the pair of guide pieces and inserting the insertion part of the endoscope into the first sleeve part and the second sleeve part through the pair of guide pieces;
extracting the balloon, the balloon mounting jig, and the insertion part of the endoscope from the container;
moving the second sleeve part and the balloon mounting jig to a proximal end side of the insertion part of the endoscope in a state where the first sleeve part is fixed to the insertion part of the endoscope; and
removing the balloon mounting jig from the second sleeve part and mounting the balloon on the insertion part of the endoscope.

* * * * *